US007056911B1

(12) United States Patent
Rosowsky

(10) Patent No.: US 7,056,911 B1
(45) Date of Patent: Jun. 6, 2006

(54) DIBENZ[B,F]AZEPINE COMPOUNDS, PHARMACEUTICAL COMPOSITIONS COMPRISING SAME AND METHODS OF USE THEREOF

(75) Inventor: Andre Rosowsky, Needham, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 0 days.

(21) Appl. No.: 09/890,112

(22) PCT Filed: Jan. 25, 2000

(86) PCT No.: PCT/US00/01968

§ 371 (c)(1),
(2), (4) Date: Dec. 26, 2001

(87) PCT Pub. No.: WO00/59884

PCT Pub. Date: Oct. 12, 2000

Related U.S. Application Data

(60) Provisional application No. 60/117,321, filed on Jan. 26, 1999.

(51) Int. Cl.
*C07D 401/06* (2006.01)
*C07D 475/04* (2006.01)
*C07D 487/04* (2006.01)
*A61K 31/55* (2006.01)
*A61P 33/08* (2006.01)

(52) U.S. Cl. ...................... 514/217; 540/588; 540/589; 540/590; 540/591; 540/592

(58) Field of Classification Search ................. 540/588, 540/589, 590, 591, 592; 514/217
See application file for complete search history.

(56) References Cited

U.S. PATENT DOCUMENTS 4,962,200 A * 10/1990 Kihara et al. ................ 544/333

FOREIGN PATENT DOCUMENTS

| CH | 372675 | * | 12/1963 |
| CH | 376 920 | A | 4/1964 |
| DE | 437 974 | C | 12/1926 |
| DE | 842 943 | C | 7/1952 |
| EP | 549352 | A2 * | 6/1993 |
| GB | 818 269 | A | 8/1959 |
| GB | 822592 | * | 10/1959 |
| JP | 8-119920 | * | 5/1996 |

OTHER PUBLICATIONS

Marangos, Paul J.; Post, Robert M.; Patel, Jitendra; Zander, Karl; Parma, Alexandra; Weiss, Susan, European Journal of Pharmacology, 93(3–4), 175–82 (English) 1983.*
Andreani, A.; Rambaldi, M.; Locatelli, A.; Aresca, P.; Bossa, R.; Galatulas, I., European Journal of Medicinal Chemistry, 26(1), 113–16 (English) 1991.*

"The Condensed Chemical Dictionary, Ninth Ed." Gesser G. Hawley, Van Nostrand, New York, 1977 , pp. 27 and 650.*
Garforth, Jacqueline; Yin, Hong; McKie, James H.; Douglas, Kenneth T.; Fairlamb, Alan H., Journal of Enzyme Inhibition, 12(3), 161–173 (English) 1997.*
Wolff, Manfred E. "Burger's Medicinal Chemistry, 4ed, Part 1", John Wiley & Sons, 1979, pp. 321–323 and 468–469.*
RM Corwin and Julie Nahm, University of Missouri College of Veterinary Medicine, 1997..*
S. Schurmann et al., "Twice–weekly Pyrimethamine–sulfadoxine Effectively Prevents *Pneumocystis carinil* Pneumionia Relapse and *Toxoplasmic encephalitis* in Patients with AIDS," J. of Infection (2001) 42, 8–15.
D. Podzamezer, M.D., "intermittent Trimethoprisim–Sulfamethoxzole Compared with Dapsone–Pyrimethamine for the Simultaneous Primary Prophylaxis of *Pneumocystis pneumonia* and Toxoplasmosis in Patients Infected with HIV," Ann. Intern. Med 1995; 122: 755–761.
M.A. Fischl, "Safety and Efficacy of Sulafmethoxazole and Trimethoprim Chemoprophylaxis for *Pneumocysitis carinii* Pneumonia in AIDS," JAMA 1998, vol. 259, No. 8.
Cremieux et al., Res. Microbiol., 146:73–83 (1995).
Patent Abstract of Japan, vol. 014, No. 304 (1990).
Database Crossfire Beilstein, Database Accession No. 4457315, XP002206576 (1982).
Database Crossfire Beilstein, Database Accession No. 753200, XP002206577 (1961).
Database Crossfire Beilstein, Database Accession No. 28740, XP002206578 (1957).
S. Schumann et al., "Twice–weekly Pyrimethamine–sulfadoxine Effectively Prevents Pneumocystis carinil Pneumonia Relapse and Toxoplasmic Encephalitis in Patients with AIDS," J. of Infection (2001) 42, 8–15.
D. Podzamezer, M.D., "Intermittent Trimethoprism–Sulfamethoxzole Compared with Dapsone–Pyrimethamine for the Simultanous Primary Prophylaxis of Pneumocystis Pneumonia and Toxoplasmosis in Patients Infected with HIV," Ann. Intern. Med 1995; 122: 755–761.
M.A. Fischi, "Safety and Efficacy of Sulfamethoxazole and Trimethoprim Chemoprophylaxis for Pneumocysitis carinii Pneumonia in AIDS," JAMA 1998, vol. 259, No. 8.

* cited by examiner

*Primary Examiner*—Thomas C. McKenzie
(74) *Attorney, Agent, or Firm*—Peter F. Corless; John B. Alexander; Edwards & Angell, LLP

(57) ABSTRACT

The invention relates to pharmaceutically active compounds, and methods of treatment and pharmaceutical compositions that utilize or comprise one or more such compounds. Compounds of the invention and particularly useful for the treatment or prophylaxis of diseases associated with parasitic infection such as pneumocystis pneumonia, toxoplasmosis, cryptosporidiosis, leischmaniasis and malaria.

31 Claims, No Drawings

DIBENZ[B,F]AZEPINE COMPOUNDS, PHARMACEUTICAL COMPOSITIONS COMPRISING SAME AND METHODS OF USE THEREOF

This application is the national stage entry of PCT/US00/01968 with international filing date of Jan. 25, 2000, which claims priority from Provisional Application 60/117,321, filed Jan. 26, 1999.

This invention was made with government support under Grant No. RO1A129904 awarded by the National Institutes of Health. The government has certain rights in this invention.

BACKGROUND OF THE INVENTION

1. Field of the Invention

The present invention relates to pharmaceutically active compounds, and methods of treatment and pharmaceutical compositions that utilize or comprise one or more such compounds. Compounds of the invention are particularly useful for the treatment or prophylaxis of diseases associated with parasitic infection, such as toxoplasmosis, cryptosporidiosis, leischmaniasis and malaria.

2. Background

Parasitic-related diseases are highly prevalent and often difficult to treat. For example, toxoplasmosis, caused by the parasitic protozoan *Toxoplasma gondii*, is a leading cause of morbidity and morality in patients with AIDS as well as in other immunocompromised patients such as persons receiving immunosuppressive cancer chemotherapy. Toxoplasmosis also is suffered by the developing fetus with the potential result of severe neurological damage. The disease is also problematic for livestock and other domesticated animals. For example, toxoplasmosis causes spontaneous abortion in sheep.

Pneumocytis pneumonia, cryptosporidiosis, leischmaniasis and malaria also result from parasitic infection and can be difficult to treat, particularly in immunocompromised subjects. Pneumocytis pneumonia results from infection by *Pneumocystis carinii*, a fungal parasite which is benign in immunocomponent individuals but can be life-threatening in patients with AIDS. Cryptosporidiosis results from infection of protozoa of the genus *Cryptosporidium* and, in the case of immunocompromised individuals, the disease can be chronic and life threatening. Leischmaniasis is any of a group of conditions resulting from *Leishmania* infection. Manifestations of leischmaniasis are significantly enhanced in the immunocompromised. Malaria can result from infection of several different parasites: *Plasmodium vivax, P. falciparum, P. malarie,* and *P. ovale.* See generally *The Merck Manual,* 16$^{th}$ edition.

Current therapies to treat toxoplasmosis and other parasitic infections have included use of trimethoprim and pyrimethamine. See *Merck Index* 8169 and 9840 (12$^{th}$ edition.). However, these agents are often not sufficiently potent to be fully effective when used alone and, consequently, the agents are typically administered in combination with a sulfa drug.

That combination drug therapy, however, has clear shortcomings. Many patients exhibit severe allergic reactions to sulfa drugs, and the therapy must be discontinued prior to effective treatment of the disease.

It thus would be desirable to have new therapies to treat parasitic related diseases, such as toxoplasmosis, cryptosporidiosis, leischmaniasis and malaria.

SUMMARY OF THE INVENTION

I have now found new compounds that exhibit significant anti-parasitic activity and will be useful to treat subjects suffering from or susceptible to various parasitic related disorders and diseases, including but not limited to toxoplasmosis, cryptosporidiosis, leischmaniasis and/or malaria.

More specifically, in a first aspect, compounds of the following Formula I are provided:

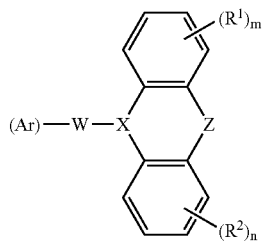

wherein Ar is optionally substituted carbocyclic aryl or optionally substituted heteroaromatic;

W is a chemical bond, optionally substituted amino (e.g. —NH—), an optionally substituted alkylene group preferably having 1 to about 3 carbons, more preferably 1 or 2 carbon atoms such as —$CH_2$— or —$CH_2CH_2$—, or aminoalkylene having 1 nitrogen and 1 or 2 carbon atoms (e.g. —$CH_2NH$—);

X is nitrogen or carbon;

Z represents a chemical bond (i.e. a direct bridge to provide a carbazole), optionally substituted methylene or ethylene (i.e. optionally substituted —$CH_2$— or —$CH_2CH_2$—), optionally substituted vinyl (i.e. optionally substituted —CH=CH—), optionally substituted azamethinyl, optionally substituted azamethylene, O, S, or optionally substituted N, or Z represents hydrogens or other non-linked substituents on each phenyl group (i.e. Z is not a bridge group to thereby provide a diphenylamine);

each $R^1$ and $R^2$ independently may be halogen; amino; hydroxy; nitro; azido; optionally substituted alkyl preferably having 1 to about 12 carbon atoms; optionally substituted alkenyl preferably having 2 to about 12 carbon atoms; optionally substituted alkynyl preferably having 2 to about 12 carbon atoms; optionally substituted alkoxy preferably having 1 to about 12 carbon atoms; optionally substituted aminoalkyl preferably having 1 to about 12 carbon atoms; optionally substituted alkanoyl optionally having 1 to about 12 carbon atoms; optionally substituted alkylthio preferably having 1 to about 12 carbon atoms; optionally substituted alkylsulfinyl preferably having 1 to about 12 carbon atoms; optionally substituted alkylsulfonyl preferably having 1 to about 12 carbon atoms; optionally substituted carbocyclic aryl; or optionally substituted hetemaromatic or heteroalicyclic preferably having from 1 to 3 separate or fused rings and with 1 to 3 hetero (N, O or S) atoms;

m and n are each independently an integer of from 0 (where a ring is fully-hydrogen substituted) to 4; and pharmaceutically acceptable salts thereof.

As discussed above, Z in the above Formula I can be non-linked hydrogen or other substituents on each phenyl group, such as compounds of the following Formula IA:

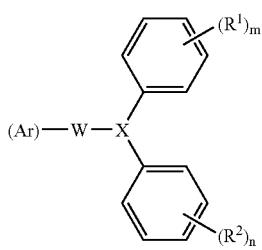

wherein in Formula IA, Ar, X, W, $R^1$ and $R^2$ are the same as defined above for Formula I; and m and n are each independently an integer of from 0 (where a ring is fully-hydrogen substituted) to 5; and pharmaceutically acceptable salts thereof.

Preferred compounds of the invention include those of Formula I where W is optionally substituted alkylene, particularly $C_{1-3}$alkylene, or optionally substituted nitrogen, even more preferably compounds of the following Formula II or IIA:

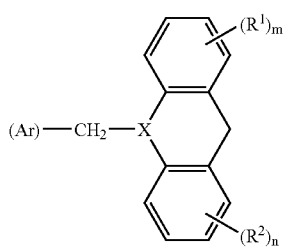

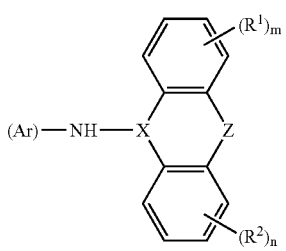

wherein in Formulae II and IIA, Ar, Z, $R^1$, $R^2$, m and n are each the same as defined above for Formula I; and pharmaceutically acceptable salts thereof.

Preferred compounds of the invention also include those where the aryl group (Ar) is a single or fused group, such as compounds of the following Formula III:

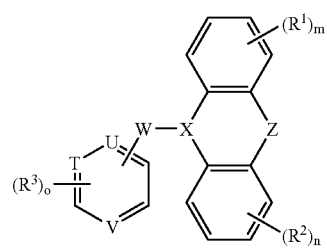

wherein in Formula III, T, U and V are each independently optionally substituted carbon, or optionally substituted nitrogen;

each $R^3$ is independently selected from the same group of substituents as identified above for $R^1$ and $R^2$; or two $R^3$ groups on adjacent ring atoms are taken together to form a fused carbocyclic aryl, heteroaromatic, cycloalkyl or heteroalicyclic ring having from 5 to about 7 ring member, o is an integer of from 0 (where the ring is fully hydrogen substituted) to 5; W, X, $R^1$, $R^2$, m and n are each the same as defined above for Formula I; and pharmaceutically acceptable salts thereof.

Particularly preferred compounds of the invention include those of the following Formulae IV and IVA:

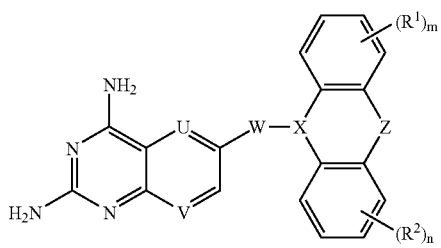

wherein in each of Formulae IV and IVA, U and V are each independently optionally substituted carbon, or optionally substituted nitrogen;

Z, X, W, $R^1$, $R^2$, m and n are each the same as defined above for Formula I; and pharmaceutically acceptable salts thereof.

As mentioned above, compounds of the invention (i.e. compounds of Formulae I, IA, II, IIA, III, IV and IVA) are useful for a number of therapeutic applications. In particular, the invention includes methods for treatment and/or prophylaxis of parasitic related diseases, including diseases or disorders associated with *Toxoplasma gondii, Pneumocystis carinii, Cryptosporidium* including *Cryptosporidium parvum, Leishmania, Plasmodium vivax, P. falciparum, P. malarie*, and/or *P. ovale* infections. Compounds of the invention also will be useful for treatment and/or prophylaxis against *tuberculosis*, particularly in immunocompromised patients, such as AIDS patients, who may have enhanced susceptibility to *tuberculosis*. The treatment methods of the invention in general comprise administration of a therapeutically effective amount of a compound of the invention to a patient in need thereof.

Compounds of the invention are especially useful for treatment of a mammal, particularly a primate such as a human, suffering from or susceptible to toxoplasmosis. Compounds of the invention also are useful for treatment of a mammal, particularly a primate such as a human, suffering from or susceptible to other parasite-related diseases and disorders such as cryptosporidiosis, leischmaniasis and malaria.

Compounds of the invention are particularly useful for treatment of subjects that are susceptible to such parasitic related disorders and diseases, i.e. prophylactic treatment. For instance, compounds of the invention may be administered as prophylactic treatment to AIDS patients and patients receiving immunosuppressive cancer treatments, who are particularly susceptible to toxoplasmosis, cryptosporidiosis, leischmaniasis and other parasitic related disorders and diseases. Unless otherwise indicated, references herein to "treatment," "therapy," or the like are inclusive of treating a subject that is suffering from a targetted disease or disorder, as well as prophylactic treatment, i.e. treating a subject that may be susceptible to such a disorder or disease.

Particularly preferred compounds of the invention exhibit inhibition activity in a standard dihydrofolate reductase assay e.g. as disclosed in Example 72 which follows. References herein to a "standard dihydrofolate reductase assay" refer to an assay of the protocol set forth in that Example 72 which follows, and which includes spectrophotometric assay of dihydrofolate redutase without test compound (control) and then such assay of dihydrofolate redutase in the presence of varying concentrations of test compound.

Without being bound by theory, it is believed compounds of the invention can exhibit potent and selective anti-parasitic activity upon administration to a subject due to the presence of the two fused or unfused phenyl groups (i.e. the phenyl groups that are optionally substituted by $R^1$ and $R^2$ in Formula I above). See, for instance, the results set forth in Example 72 which follows. More particularly, it is believed that one of those phenyl groups can interact hydrophobically with lipophilic amino acid residues in the active site of dihydrofolate reductase in both the parasite and host, only the active site of the parasite enzyme is sufficiently spacious to accommodate both phenyl groups of compounds of the invention, thereby providing for selective treatment against the parasite.

The invention also provides pharmaceutical compositions that comprise one or more compounds of the invention and a suitable carrier for the compositions.

Other aspects of the invention are disclosed infra.

DETAILED DESCRIPTION OF THE INVENTION

As discussed above, we have now discovered that compounds of the following Formula I, IA, II, IIA, III, IV and IVA (i.e. compounds of the invention) are useful for therapeutic applications, particularly against parasitic-related diseases and disorders.

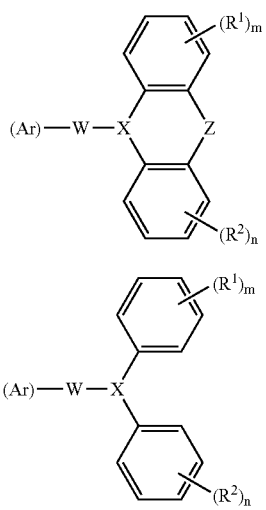

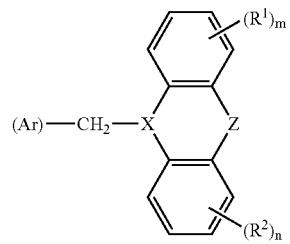

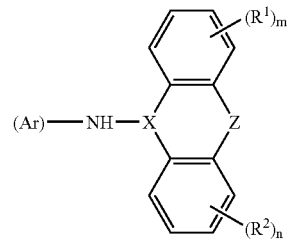

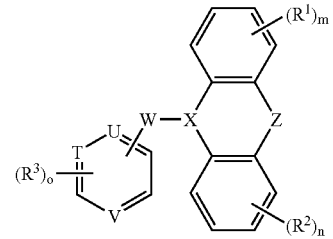

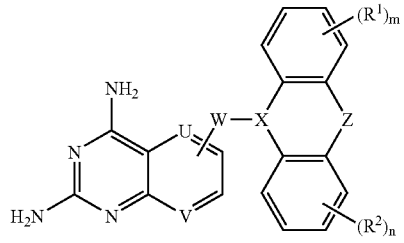

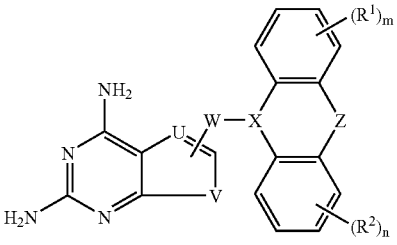

wherein Ar, W, X, Z, $R^1$, $R^2$, $R^3$, T, U, V, m, n and o are as defined above.

Preferred compounds of the invention are amino pyrimidine compounds, particularly 2,4-diaminopyrimidine and condensed 2,4-diaminopyrimidine compounds.

Suitable halogen substituent groups of compounds of Formulae I, IA, II, IIA, III, IV and IVA, as defined above (i.e. compounds of the invention) include F, Cl, Br and I. Alkyl groups of compounds of the invention typically have from 1 to about 12 carbon atoms, more preferably 1 to about 8 carbon atoms, still more preferably 1 to about 6 carbon atoms, even more preferably 1, 2, 3 or 4 carbon atoms, or still more preferably 1, 2 or 3 carbon atoms. As used herein, the term alkyl unless otherwise modified refers to both cyclic and noncyclic groups, although of course cyclic groups will comprise at least three carbon ring members.

Preferred alkenyl and alkynyl groups of compounds of the invention have one or more unsaturated linkages and typically from 2 to about 12 carbon atoms, more preferably 2 to about 8 carbon atoms, still more preferably 2 to about 6 carbon atoms, even more preferably 1, 2, 3 or 4 carbon atoms. The terms alkenyl as used herein refers to both cyclic and noncyclic groups, although straight or branched noncyclic groups are generally more preferred. The term alkynyl as used herein refers to straight or branched alkynyl groups. Preferred alkoxy groups of compounds of the invention include groups having one or more oxygen linkages and from 1 to about 12 carbon atoms, more preferably from 1 to about 8 carbon atoms, and still more preferably 1 to about 6 carbon atoms, even more preferably 1, 2, 3 or 4 carbon atoms. Preferred alkylthio groups of compounds of the invention include those groups having one or more thioether linkages and from 1 to about 12 carbon atoms, more preferably from 1 to about 8 carbon atoms, and still more preferably 1 to about 6 carbon atoms. Alkylthio groups having 1, 2, 3 or 4 carbon atoms are particularly preferred. Preferred alkylsulfinyl groups of compounds of the invention include those groups having one or more sulfoxide (SO) groups and from 1 to about 12 carbon atoms, more preferably from 1 to about 8 carbon atoms, and still more preferably 1 to about 6 carbon atoms. Alkylsulfinyl groups having 1, 2, 3 or 4 carbon atoms are particularly preferred. Preferred alkylsulfonyl groups of compounds of the invention include those groups having one or more sulfonyl ($SO_2$) groups and from 1 to about 12 carbon atoms, more preferably from 1 to about 8 carbon atoms, and still more preferably 1 to about 6 carbon atoms. Alkylsulfonyl groups having 1, 2, 3 or 4 carbon atoms are particularly preferred. Preferred aminoalkyl groups include those groups having one or more primary, secondary and/or tertiary amine groups, and from 1 to about 12 carbon atoms, more preferably 1 to about 8 carbon atoms, still more preferably 1 to about 6 carbon atoms, even more preferably 1, 2, 3 or 4 carbon atoms. Secondary and tertiary amine groups are generally more preferred than primary amine moieties. Suitable heteroaromatic groups of compounds of the invention contain one or more N, O or S atoms and 1–3 separate or fused rings and include, e.g., coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazol. Optionally substituted pteridine is a particularly preferred Ar group of compounds of Formula I, IA, II, and III (i.e. in Formula III U and V are each nitrogen, and two $R^3$ groups are taken together to form a pteridine group), particularly pteridine substituted at the 6 position to the W group linkage. Suitable heteroalicyclic groups of compounds of the invention contain one or more N, O or S atoms and 1–3 separate or fused rings and include, e.g., tetrahydrofuranyl, thienyl, tetrahydropyranyl, piperidinyl, morpholino and pyrrolindinyl groups. Suitable carbocyclic aryl groups of compounds of the invention include single and multiple ring compounds, including multiple ring compounds that contain separate and/or fused aryl groups. Typical carbocyclic aryl groups of compounds of the invention contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl.

Suitable aralkyl groups of compounds of the invention include single and multiple ring compounds, including multiple ring compounds that contain separate and/or fused aryl groups. Typical aralkyl groups contain 1 to 3 separate or fused rings and from 6 to about 18 carbon ring atoms. Preferred aralkyl groups include benzyl and methylenenaphthyl (—$CH_2$-naphthyl), and other carbocyclic aralkyl groups, as discussed above.

As discussed above, W groups of Formulae I, IA, III, IV and IVA suitably are optionally substituted $C_{1-3}$ alkylene, more preferably $CH_2$ or $CH_2CH_2$, or an optionally substituted amino such as —NH—, —NH($CH_3$)—, etc., or optionally substituted aminoalkylene such as —$CH_2$NH—, —NH$CH_2$—, —$CH_2CH_2$NH—, —NH$CH_2CH_2$—, or —$CH_2$NH$CH_2$—, carbon atoms, still more preferably 1, 2 or 3 carbon atoms.

Particularly preferred Z groups of Formula I, II, IIA, III, IV and IVA include —$CH_2$—, —$CH_2CH_2$—, —CH═CH—, NH, O and S, with —CH═CH— being particularly preferred.

Specifically preferred compounds of the invention include the following:

N-(2,4-diaminopteridin-6-yl)methyl-N,N-diphenylamine;
(2,4-diamino-6-(carbazol-5-yl)methylpteridine;
2,4-diamino-6-(9,10-dihydroacridin-9-yl)methylpteridine;
N-[(2,4-diaminopteridin-6-yl)methyl]phenoxazine;
N-[(2,4-diaminopteridin-6-yl)methyl]phenothiazine;
N-[(2,4-diaminopteridin-6-yl)methyl]-9,10-dihydrodibenz[b,f]azepine;
N-[(2,4-diaminopteridin-6-yl)methyl]dibenz[b,f]azepine;
N-[(2,4-diaminopyrido[2,3-d]pyrimidin-6-yl)methyl]-N,N-diphenylamine;
N-[(2,4-diaminopyrido[3,2-d]pyrimidin-6-yl)methyl]-N,N-diphenylamine;
N-[(2,4-diaminoquinazolin-6-yl)methyl]-N,N-diphenylamine;
N-[(2,4-diaminothieno[2,3-d]pyrimidin-5-yl)methyl]-N,N-diphenylamine;
N-[(2,4-diaminofuro[2,3-d]pyrimidin-5-yl)methyl]-N,N-diphenylamine;
N-[(2,4-diaminopyrimidin-6-yl)methyl-N,N-diphenylamine;
N-[(2,4-diaminopteridin-6-yl)methyl]carbazole;
N-[(2,4-diaminopyrido[2,3-d]pyrimidin-6-yl)methyl]carbazole;
N-[(2,4-diaminopyrido[3,2-d]pyrimidin-6-yl)methyl]carbazole;
N-[(2,4-diaminoquinazolin-6-yl)methyl]carbazole;
N-[(2,4-diaminothieno[2,3-d]pyrimidin-5-yl)methyl]carbazole;
N-[(2,4-diaminofuro[2,3-d]pyrimidin-5-yl)methyl]carbazole;
N-[(2,4-diaminopyrimidin-6-yl)methyl]carbazole;
N-[(2,4-diaminopteridin-6-yl)methyl]-9,10-dihydroacridine;
N-[(2,4-diaminopyrido[2,3-d]pyrimidin-6-yl)methyl]-9,10-dihydroacridine;
N-[(2,4-diaminopyrido[3,2-d]pyrimidin-6-yl)methyl]-9,10-dihydroacridine;
N-[(2,4-diaminoquinazolin-6-yl)methyl]-9,10-dihydroacridine;
N-[(2,4-diaminothieno[2,3-d]pyrimidin-5-yl)methyl]-9,10-dihydroacridine;
N-[(2,4-diaminofuro[2,3-d]pyrimidin-5-yl)methyl]-9,10-dihydroacridine;
N-[(2,4-diamiopyrimidin-6-yl)methyl]-9,10-dihydroacridine;
N-[(2,4-diaminopteridin-6-yl)methyl]phenoxazine;
9-[(2,4-diaminopyrido[2,3-d]pyrimidin-6-yl)methyl] phenoxazine;

9-[(2,4-diaminopyrido[3,2-d]pyrimidin-6-yl)methyl]
  phenoxazine;
9-[(2,4-diaminoquinazolin-6-yl)methyl]pbenoxazine;
9-[(2,4-diaminothieno[2,3-d]pyrimidin-5-yl)methyl]
  phenoxazine;
9-[(2,4-diaminofuro[2,3-d]pyrimidin-5-yl)methyl]
  phenoxazine;
9-[(2,4-diaminopyrimidin-6-yl)methyl]phenoxazine;
N-[(2,4-diaminopteridin-6-yl)methyl]phenothiazine;
9-[(2,4-diaminopyrido[2,3-d]pyrimidin-6-yl)methyl]
  phenothiazine;
9-[(2,4-diaminopyrido[3,2-d]pyrimidin-6-yl)methyl]
  phenothiazine;
9-[(2,4-diaminoquinazolin-6-yl)methyl]phenothiazine;
9-[(2,4-diaminothieno[2,3-d]pyrimidin-5-yl]phenothiazine;
9-[(2,4-diaminofuro[2,3-d]pyrimidin-5-yl)methyl]
  phenothiazine;
9-[(2,4-diaminopyrimidin-5-yl)methyl]phenothiazine,
N-[(2,4-diaminopteridin-6-yl)methyl]-9,10-dihydrodibenz
  [b,f]azepine;
N-[(2,4-diaminopyrido[2,3-d]pyrimidin-6-yl)methyl]-9,10-
  dihydrodibenz[b,f]azepine;
N-[(2,4-diaminopyrido[3,2-d]pyrimidin-6-yl)methyl]-9,10-
  dihydrodibenz[b,f]azepine;
9-[(2,4-diaminoquinazolin-6-yl)methyl]-9,10-
  dihydrodibenz[b,f]azepine;
9-[(2,4-diaminothieno[2,3-d]pyrimidin-5-yl)methyl]-9,10-
  dihydrodibenz[b,f]azepine;
9-[(2,4-diaminofuro[2,3-d]pyrimidin-5-yl)methyl]-9,10-
  dihydrodibenz[b,f]azepine;
9-[(2,4-diaminopyrimidin-5-yl)methyl]-9,10-dihydrodibenz
  [b,f]azepine;
N-[(2,4-diaminopteridin-6-yl)methyl]dibenz[b,f]azepine;
9-[(2,4-diaminopyrido[2,3-d]pyrimidin-6-yl)methyl]dibenz
  [b,f]azepine;
9-[(2,4-diaminopyrido[3,2-d]pyrimidin-6-yl)methyl]dibenz
  [b,f]azepine;
9-[(2,4-diaminoquinazolin-6-yl)methyl]dibenz[b,f]azepine;
9-[(2,4-diaminothieno[2,3-d]pyrimidin-5-yl)methyl]dibenz
  [b,f]azepine;
9-[(2,4-diaminofuro-2,3-d]pyrimidin-5-yl)methyl]dibenz[b,
  f]azepine;
9-[(2,4-diaminopyrimidin-6-yl)methyl]dibenz[b,f]azepine;
N-(2,4-diaminopyrido[2,3-d]pyrimidin-6-yl)
  benzhydrylamine;
N-(2,4-diaminoquinazolin-6-yl)benzhydrylamine;
N-[(2,4-diaminopyrimidin-5-yl)methyl]benzhydrylamine;
N-[(2,4-diaminopyrimidin-5-yl)ethyl]benzhydrylamine;
9-[N-(2,4-diaminoquinazolin-6-yl)amino]fluorene;
9-[N-(2,4-diaminoquinazolin-5-yl)methylamino]fluorene;
9-[N-[2-(2,4-diaminoquinazolin-5-yl)ethyl]amino]fluorene;
5-[(N-(2,4-diaminopyrido[2,3-d]pyrimidin-6-yl)amino]-
  5H-10,11-dihydrodibenzo[a,d]cycloheptene;
5-[N-(2,4-diaminoquinazolin-6-yl)amino]-5H-10,11-
  dihydrodibenzo[a,d]cycloheptene;
5-[N-(2,4-diaminopyrimidin-5-yl)methylamino]-5H-10,11-
  dihydrodibenzo[a,d]cycloheptene;
5-[N-[2-(2,4-diaminopyrimidin-5-yl)ethyl]amino]-5H-10,
  11-dihydrodibenzo[a,d]cycloheptene;
5-[N-(2,4-diaminopyrimidin-[2,3-d]pyrimidin-6-yl)amino]-
  5H-dibenzo[a,d]cycloheptene;
5-[N-(2,4-diaminoquinazolin-6-yl)amino]-5H-dibenzo[a,d]
  cycloheptene;
5-[N-(2,4-diaminopyrimidin-5-yl)methylamino]-5H-
  dibenzo[a,d]cycloheptene; and
5-[N-[2-(2,4-diaminopyrimidin-5-yl)ethyl]amino]5H-
  dibenzo[a,d]cycloheptene; and pharmaceutically acceptable salts thereof.

Compounds of the invention may be readily prepared. For instance, a suitable aryl compound (Ar group precursor) linked to W group precursor that has a reactive carbon (e.g. a carbon substituted with a suitable leaving group such as halogen e.g. Br or I) can be reacted in the presence of a hydride or other suitable base with a fused ring compound, or a diphenyl amine to provide compounds of the invention. Thus, for example, to synthesize compounds of Formula I where Z is a chemical bond and W is alkylene, an optionally substituted carbazole may be reacted in the presence a molar excess of sodium hydride with a haloalkylaryl compound. To synthesize compounds where W is optionally substituted amino or aminoalkylene, the corresponding aryl compound can be employed, e.g. an aminoaryl or alkylaminoaryl compound, can be employed. To prepare compounds where X is a hetero atom, a phenoxazine, phenothiazine or phenazine can be reacted under similar conditions. A diphenylamine can be reacted to provide compounds of Formula IA. See the examples which follow for exemplary reaction conditions.

As discussed above, preferred compounds of the invention exhibit good inhibition activity in a standard dihydrofolate reductase assay. In particular, preferred compounds of the invention exhibit in a standard dihydrofolate reductase assay an $IC_{50}$ (:M) of less than about 50 against rat liver dihydrofolate reductase, and other mammalian including human dihydrofolate reductase; more preferably an $IC_{50}$ (:M) of less than about 25 against rat liver dihydrofolate reductase, and other mammalian including human dihydrofolate reductase; even more preferably an $IC_{50}$ (:M) of less than about 10 against rat liver dihydrofolate reductase, and other mammalian including human dihydrofolate reductase.

Preferred compounds of the invention also include those that exhibit in a standard dihydrofolate reductase assay an $IC_{50}$ (:M) of less than about 20 against *P. carinii* dihydrofolate reductase, more preferably an $IC_{50}$ (:M) of less than about 10 against *P. carinii* dihydrofolate reductase, still more preferably an $IC_{50}$ (:M) of less than about 5 against *P. carinii* dihydrofolate reductase, even more preferably an $IC_{50}$ (:M) of less than about 1 or 2 against *P. carinii* dihydrofolate reductase. Preferred compounds of the invention also exhibit in a standard dihydrofolate reductase assay an $IC_{50}$ (:M) of less than about 10 against *T. gondii* dihydrofolate reductase, more preferably an $IC_{50}$ (:M) of less than about 5 against *T. gondii* dihydrofolate reductase, still more preferably an $IC_{50}$ (:M) of less than about 1 against *T. gondii* dihydrofolate reductase, even more preferably an $IC_{50}$ (:M) of less than about 0.1 against *T. gondii* dihydrofolate reductase.

Particularly preferred compounds of the invention include those compounds that exhibit selective activity for a targeted disorder or microorganism relative to activity against host proliferative tissue (e.g. bone marrow, oral/intestinal mucosa and the like).

Compounds of the invention may be used in therapy in conjunction with other medicaments. For example, compounds of the invention may be administered in combination with agents used for treatment against parasitic infections and associated diseases and disorders. For instance, compounds of the invention can be administered in conjunction with a sulfa drug such as sulfacetamide, sulfadiazine, sulfadimethoxine, sulfadimidine, sulfamethoxazole, sulfathiazole, sulfaguanidine and the like. However, preferred compounds of the invention will be sufficiently potent to enable effective therapy without use of another active pharmaceutical agent.

Compounds of the invention can be suitably administered to a subject by a variety of routes including oral, parenteral (including intraperitoneal, subcutaneous, intravenous, intradermal or intramuscular injection), topical (including trasdermal, buccal or sublingal), or nasal. Administration also suitably may be via inhalation or rectally. The optimal dose can be determined by conventional means.

Compounds of the present invention are suitably administered to a subject in the protonated and water-soluble form, e.g., as a pharmaceutically acceptable salt of an organic or inorganic acid, e.g., hydrochloride, sulfate, hemi-sulfite, phosphate, nitrate, acetate, oxalate, citrate, maleate, mesylate, etc., or if an acid group is present on the therapeutic compound, a base addition salt can be employed, e.g. a Na or K salt.

Compounds of the invention can be employed, either alone or in combination with one or more other therapeutic agents as discussed above, as a pharmaceutical composition in mixture with conventional excipient, i.e., pharmaceutically acceptable organic or inorganic carrier substances suitable for parenteral, oral, enteral, topical or intranasal application which do not deleteriously react with the active compounds and are not deleterious to the recipient thereof. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds.

For parenteral application, particularly suitable are solutions, preferably oily or aqueous solutions as well as suspensions, emulsions, or implants, including suppositories. Ampules are convenient unit dosages.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed Sustained release compositions can be formulated including those wherein the active component is protected with differentially degradable coatings, e.g., by microencapsulation, multiple coatings, etc.

As discussed above, the compounds of this invention are particularly useful in the treatment of mammalian subjects, e.g. primates particularly humans, to provide treatment from infection a variety of microorganisms including *Toxoplasma gondii, Pnemocytis carinii, Cryptosporidium* including *Cryprosporidium parvum, Leishmania, Plasmodium vivax, P. falciparum, P. malarie,* and *P. ovale.* Such subjects include those afflicted with toxoplasmosis, cryptosporidiosis, leischmaniasis or malaria Such subjects often will be immunocompromised, e.g. the subjects may suffer a primary infection from a retrovirus such as human immunodeficiency virus. The patients also may be immunocompromised as a result of other circumstances, e.g. due to cancer therapy.

Compounds of the invention also will be useful for veterinary applications, e.g. to treat mammals such as livestock e.g. cattle, sheep, goats, cows, swine and the like and dogs and cats and other pets and domesticated animals; poultry such as chickens, ducks, geese, turkeys and the like. In particular, the compounds will be useful to treat animals that may carry *T. gondii* such as sheep, pigs and cats.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines. In general, a suitable effective dose of one or more compounds of Formulae I, IA, II, IIA, III, IV, IVA, will be in the range of from 0.01 to 100 milligrams per kilogram of bodyweight of recipient per day, preferably in the range of from 0.01 to 20 milligrams per kilogram bodyweight of recipient per day, more preferably in the range of 0.05 to 4 milligrams per kilogram bodyweight of recipient per day. The desired dose is suitably administered once daily, or several sub-doses, e.g. 2 to 4 sub-doses, are administered at appropriate intervals through the day, or other appropriate schedule.

All documents mentioned herein are incorporated herein by reference in their entirety. The following non-limiting examples are illustrative of the invention.

EXAMPLE 1

N-(2,4-Diaminopteridin-6-yl)methyl-N,N-diphenylamine (Formula I: Ar=2,4-diaminopteridin-6-yl); X=N; W=CH$_2$; Z=non-linked hydrogens on each phenyl group; m=n=0).

Powdered NaH (50 mg, 2.1 mmol) is added to a stirred solution of diphenylamine (1.3 g, 0.77 mmol) in dry THF (10 mL) at 0° C. under N$_2$. After 10 min, 2,4-diamino-6-bromomethylpteridine hydrobromide (100 mg, 0.3 mmol) is added and the reaction mixture is allowed to come to room temperature and left to stir for 2 days. The excess NaH is decomposed with MeOH (1 mL) and the mixture is concentrated to dryness by rotary evaporation. Flash chromatography on silica gel with 95:5 CHCl$_3$-MeOH as the eluent affords the product, N-(2,4-diaminopteridin-6-yl)methyl-N, N-diphenylamine, as a bright-yellow powder (56 mg, 54% yield); mp >250° C. dec.; MS (FAB) m/z (M+1)=344; IR (KBr) v 3450, 3340, 3170, 1630, 1590, 1550, 1490, 1450, 1360, 1220 cm$^{-1}$; $^1$H NMR(d$_6$-DMSO) δ 5.10 (s, 2H, CH$_2$), 6.70 (m, 10H, aromatic), 8.60 (s, 1H, C$_7$-H. Anal. Calcd for C$_{19}$H$_{17}$N$_7$.0.8H$_2$O: C, 63.73; H, 5.23; N, 27.40. Found: C, 64.15; H, 4.85; N, 27.07.

EXAMPLE 2

Preparation of 2,4-Diamino-6-(carbazol-5-yl) methylpteridine (Formula I: Ar=6-(2,4-diaminopteridine); X=N; W=CH$_2$; Z=chemical bond; m=n=0).

NaH (60% oil suspension containing 44 mg, 1.88 mmol) was added to a stirred solution of carbazole (65.5 mg, 0.392 mmol) in dry THF (10 mL) at 0° C. under N$_2$. After 10 minutes, 2,4-diamino-6-bromo-methylpteridine hydrobromide (100 mg, 0.392 mmol) was added and the reaction mixture was allowed to come to room temperature and left to stir for 2 days. The excess NaH was decomposed with several drops of MeOH followed by three drops of glacial AcOH, and the mixture was concentrated to dryness by rotary evaporation Flash chromatography on silica gel with 85:15 CHCl$_3$-MeOH followed by 1:1 CHCl$_3$-MeOH as the eluent. Appropriate fractions were pooled and evaporated to a yellow solid which was dried in vacuo at 70° C. overnight, to provide the title compound, 2,3-diamino-6-(carbazol-5-yl)methylpteridine, yield 10 mg (<10%). MS (FAB) m/z (M+1)=342.2265. Anal. Calcd. for C$_{19}$H$_{15}$N$_7$1/6CHCl$_3$: C, 63.72; H, 4.23. Found: C, 63.41; H, 4.11.

EXAMPLE 3

Preparation of 2,4-Diamino-6-(9,10-dihydroacridin-9-yl) methylpteridine (Formula I: Ar=6-(2,4-diaminopteridine); X=N; W=CH$_2$; Z=CH$_2$; m=n=0).

Raney Ni (1 g) was added to a solution of acridine (1 g, 5.58 mmol) in EtOH (20 mL), and the mixture was shaken under a hydrogen atmosphere (50 psi) for 2 days. Additional EtOH (200 mL) was added, and the Ni catalyst was removed by filtration. Evaporation of filtrate and recrystallization of the residue from MeOH afforded colorless needles of 5,10-dihydroacridine (0.7 g, 70% yield); mp 169–170° C. A portion of this material (0.224 g, 1.18 mmol) was dissolved in dry THF (10 mL) under N$_2$, and the solution was cooled to 0° C., and NaH (50% oil suspension containing 0.119 g, 4.7 mmol) was added in small portions with magnetic stirring After 10 min, 2,4-diamino-6-bromomethylpteridine hydrobromide (0.100 g, 0.392 mmol) was added slowly with continued stirring, and the reaction mixture was allowed to warm to room temperature and stirred overnight. Excess sodium hydride was destroyed with a small drops of AcOH, and the solvents were removed by rotary evaporation. Flash chromatography of the residue on silica gel with 9:1 ChCl$_3$-MeOH as the eluent afforded the title compound, 2,4-diamino-6-(9,10-dihydroacridin-9-yl)methylpteridine, as a yellow-brown solid (ca. 10% yield); mp>250° C. dec. MS (FAB m/z (M+1)=370.1785.

EXAMPLE 4

Preparation of N-[(2,4-Diaminopteridin-6-yl)methyl] phenoxazine (Formula I: Ar=6-(2,4-diaminopteridine); X=N; W=CH$_2$; Z=O; m=n=0).

NaH (60% oil suspension containing 51 mg, 2.0 mmol) was added to a stirred solution of phenoxazine (147 mg, 0.784 mmol) in dry THF (10 mL) at 0° C. under N$_2$. After 10 min. 2,4-diamino-6-bromomethylpteridine hydrobromide (100 mg, 0.392 mmol) was added and the reaction mixture was allowed to come to room temperature and left to stir for 2 days. The excess NaH was decomposed with MeOH (1 mL), and the mixture was concentrated to dryness by rotary evaporation. Flash chromatography on silica gel yielded the title compound, N-[(2,4-diaminopteridin-6-yl) methyl]phenoxazine, as a brown solid; yield 47 mg (34%); mp >250° C. dec. Anal. Calcd. for C$_{19}$H$_{15}$N$_7$O0.4H$_2$O: C, 62.60; H, 4.37. Found: C, 62.84; H, 4.10.

EXAMPLE 5

Preparation of N-[(2,4-Diaminopteridin-6-yl)methyl] phenothiazine (Formula I: Ar=6-(2,4-diaminopteridine); X=N; W=CH$_2$; Z=S; m=n=0).

NaH (60% oil suspension containing 51 mg, 2.0 mmol) was added to a stirred solution of phenoxazine (159 mg, 0.784 mmol) in dry THF (20 mL) at 0° C. under N$_2$. After 10 min. 2,4-diamino-6-bromomethylpteridine hydrobromide (100 mg, 0.392 mmol) was added and the reaction mixture was allowed to come to room temperature and left in stir for 2 days. The excess NaH was decomposed with MeOH (1 mL), and the mixture was concentrated to dryness by rotary evaporation. Flash chromatography on silica gel yielded the title compound, N-[(2,4-diaminopteridin-6-yl) methyl]phenothiazine, as a greenish-yellow solid; yield 20 mg (14%); mp 250° C. dec. Anal. Calcd. for C$_{19}$H$_{19}$N$_7$5/ 5CHCl$_3$; C, 64.73, H, 4.93, Found: C, 64.55; H, 4.90.

EXAMPLE 6

Preparation of N-[(2,4-Diaminopteridin-6-yl)methyl]-9, 10-dihydrodibenz[b,f]azepine (Formula I: Ar=6-(2,4-diaminopteridine); X=N; W=CH$_2$; Z=CH$_2$CH$_2$; m=n=0).

NaH (60% oil suspension containing 11 mg, 0.47 mmol) was added to a stirred solution of 9,10-dihydrodibenz[b,f] azepine (77 mg, 0.392 mmol) in dry THF (10 mL) at 0° C. under N$_2$. After 10 minutes, 2,4-diamino-6-bromomethylpteridine hydrobromide (100 mg, 0.392 mmol) was added and the reaction mixture was allowed to come to room temperature and left to stir for 2 days. After the excess NaH was decomposed with a small volume of MeOH, the mixture was poured into H$_2$O (20 mL) and the product extracted into 85:15 CHCl$_3$-MeOH (3×50 mL). The organic layer was dried over Na$_2$SO$_4$ and evaporated, and the residue was purified by preparative TLC (silica gel, 85L15 CHCl$_3$-MeOH) to obtain the title compound, N-[(2,4-diaminopteridin-6-yl)methyl]-9,10-dihydrodibenz[b,f] azepine, as a yellow solid (35 mg, 24% yield). Anal. Calcd. for C$_{21}$H$_{19}$N$_7$1/5CHCl$_3$: C, 64.73; H, 4.93. Found: C, 64.55: H, 4.90.

EXAMPLE 7

Preparation of N-[(2,4-Diaminopteridin-6-yl)methyl] dibenz[b,f]azepine (Formula I: Ar=6-(2,4-diaminopteridine); X=N; W=CH=CH; Z=CH$_2$; m=n=0).

NaH (60% oil suspension containing 44 mg, 1.88 mmol) was added to a stirred solution of dibenz[b,f]azepine (76 mg, 0.392 mmol) in dry THF (10 mL) at 0° C. under N$_2$. After 10 min, 2,4-diamino-6-bromomethylpteridine hydrobromide (100 mg, 0.392 mmol) was added and the reaction mixture was allowed to come to room temperature and left to stir for overnight After the excess NaH was decomposed with MeOH (0.5 mL) and 3 drops of glacial AcOH, the mixture was poured into H$_2$O (20 mL) and the product was extracted into 85:15 CHCl$_3$:MeOH (3×5 mL). The organic layers was dried over Na$_2$SO$_4$ and evaporated and the residue was purified by column chromatography (flash silica gel. 85:15 CHCl$_3$:MeOH) to obtain the title compound, N-[(2,4-diaminopteridin-6-yl)methyl]dibenz[b,f]azepine, as a yellow solid (25 mg, 17% yield). MS (FAB) m/z=M+1) 367.199. Anal. Calcd. for C$_{21}$H$_{17}$N$_7$ 1/4CHCl$_3$: C, 64.25; H, 4.38; N, 24.68: Found: C, 64.06; H, 4.19, N, 23.82.

EXAMPLE 8

N-[(2,4-Diaminopyrido[2,3-d]pyrimidin-6-yl)methyl]-N, N-diphenylamine (Formula I: Ar=2,4-diaminopyrido[2,3-d] pyrimidin-6-yl); X=N; W=CH$_2$; Z=non-linked hydrogens on each phenyl group; Z=CH$_2$; m=n=0) is prepared similarly as disclosed in Example 1 above by using N,N-diphenylamine (1.3 g, 0.77 mmol), NaH (50 mg, 2.1 mmol), and 2,4-diamino-6-bromomethylpyrido[2,3-d]pyrimidine hydrobromide (100 mg, 0.3 mmol). The product can be purified by chromatography.

EXAMPLE 9

N-[(2,4-Diaminopyrido[3,2-d]pyrimidin-6-yl)methyl]-N, N-diphenylamine (Formula I: Ar=2,4-diaminopyrido[3,2-d] pyrimidin-6-yl; X=N; W=CH$_2$; Z=non-linked hydrogens on each phenyl group; Z=CH$_2$; m=n=0) is prepared similarly as disclosed in Example 1 above by using diphenylamine (1.3 g, 0.77 mmol), NaH (50 mg, 2.1 mmol), and 2,4-diamino-6-bromomethylpyrido[2,3-d]pyrimidine hydrobromide (100 mg, 0.3 mmol). The product can be purified by chromatography.

EXAMPLE 10

N-[(2,4-Diaminoquinazolin-6-yl)methyl]-N,N-diphenylamine (Formula I: Ar=2,4-diaminoquinazolin-6-yl; X=N; W=CH$_2$; Z=non-linked hydrogens on each phenyl group; m=n=0) is prepared similarly as disclosed in Example 1 above by using diphenylamine (1.3 g, 0.77 mmol), NaH (50 mg, 2.1 mmol), and 2,4-diamino-6-bromomethylquinazoline hydrobromide (100 mg, 0.3 mmol). The product can be purified by chromatography.

EXAMPLE 11

N-[(2,4-Diaminothieno[2,3-d]pyrimidin-5-yl)methyl]-N,N-diphenylamine (Formula I: Ar=2,4-diaminothieno[2,3-d]pyrimidin-5-yl; W=$CH_2$; X=N; Z=non-linked hydrogens on each phenyl group; m=n=0).

Step 1.

A mixture of 2,4-diamino-5-methylthieno[2,3-d]pyrimidine (1.3 g, 7.2 mmol) and pivalic anhydride (33 g, 18 mmol) in dry pyridine is refluxed under $N_2$ overnight, then cooled and evaporated under reduced pressure. The residue is taken up in $Et_2O$ (500 mL), the solution is washed with 5% $NaHCO_3$ (2×100 mL), the organic layer is dried and evaporated, and the residue is recrystallized from $Et_2O$ to obtain the 2,4-bis(pivaloylamino) derivative.

Step 2.

The 2,4-bis(pivaloylamino) compound (2.6 g, 7.5 mmol) obtained in Step 1 is dissolved in $CHCl_3$ (600 mL), and the solution is cooled to 0° C. and treated with N-bromosuccinimide (1.6 g, 9.0 mmol) and benzoyl peroxide (0.2 g, 0.8 mmol). The solution stirred overnight at room temperature, treated with additional N-bromosuccinimide (9.1 g, 51 mmol) and benzoyl peroxide (1.2 g, 4.8 mmol), and left to stir for a total of 6 days. The yellow solid which precipitates during this time is filtered off, and the filtrate is washed with $H_2O$ (2×50 mL), dried and evaporated to obtain 2,4-bis(pivaloylamino)-5-bromomethyl-6-bromothieno[2,3-d]pyrimidine.

Step 3.

A mixture of 2,4-bis(pivaloylamino)-5-bromomethyl-6-bromothieno[2,3-d]pyrimidine prepared in Step 2 above (200 mg, 0.4 mmol), diphenylamine (1.3 g, 0.77 mmol) and NaH (50 mg, 2.1 mmol) in dry THF (10 mL) is stirred at room temperature for 2 days, the excess NaH is decomposed with MeOH (1 mL), the solvent is evaporated, and the residue is chromatographed on silica gel to obtain 2,4-bis(pivaloylamino)-5-N,N-diphenylaminomethyl)-6-bromothieno[2,3-d]pyrimidine.

Step 4.

To remove the pivaloyl groups, 2,4-bis(pivaloylamino)-5-(N,N-diphenylaminomethyl)-6-bromothieno[2,3-d]pyrimidine prepared in Step 3 above (224 mg, 0.4 mmol) is stirred in a mixture of MeOH (100 mL) and 1 N NaOH (50 mL) at 35° C. overnight. The precipitated solid is collected, washed with $H_2O$, and air-dried.

Step 5.

To remove the remaining bromine atom, a solution of the compound prepared in Step 4 above (118 mg, 0.3 mmol) in 1:1 THF-$H_2O$ (30 mL) is cooled to 0° C. and treated with $PdCl_2$ (240 mg, 0.6 mmol) and $NaBH_4$ (110 mg, 3.0 mmol). The mixture is left to stir at room temperature for 8 hrs, the THF is evaporated under reduced pressure and replaced with an equal volume of $H_2O$, and the product is extracted several times with $CHCl_3$. The combined organic layers are dried over $Na_2SO_4$ and evaporated, and the residue is purified by silica gel chromatography using a mixture of $CHCl_3$ and MeOH as the eluent to afford the desired compound, N-[(2,4-diaminothieno[2,3-d]pyrimidin-6-yl)methyl]-N,N-diphenylamine. The final product and its intermediates can be purified by chromatography.

EXAMPLE 12

N-[(2,4-Diaminofuro[2,3-d]pyrimidin-5-yl)methyl]-N,N-diphenylamine (Formula I: Ar=2,4-diaminofuro[2,3-d]pyrimidin-5-yl; W=$CH_2$; X=N; Z=non-linked hydrogens on each phenyl group; m=n=0) is prepared similarly to N-[(2,4-diaminothieno[2,3-d]pyrimidin-6-yl)methyl]-N,N-diphenylamine as disclosed in Example 11 above by using diphenylamine (1.3 g, 0.77 mmol), NaH (50 mg, 2.1 mmol), and 2,4-diamino-5-chloromethylfuro[2,3-d]pyrimidine (60 mg, 0.3 mmol). The product can be purified by chromatography.

EXAMPLE 13

N-[(2,4-Diaminopyrimidin-6-yl)methyl-N,N-diphenylamine (Formula I: Ar=2,4-diaminopyrimidin-5-yl; W=$CH_2$; X=N; Z=non-linked hydrogens on each phenyl group; m=n=0) is prepared similarly to N-(2,4-diaminopteridin-6-yl)methyl-N,N-diphenylamine as disclosed above by using diphenylamine (1.3 g, 0.77 mmol), NaH (50 mg, 2.1 mmol), and 2,4-diamino-5-bromomethylpyrimidine hydrobromide (86 mg, 0.3 mmole). The product can be purified by chromatography.

EXAMPLE 14

N-[(2,4-Diaminopteridin-6-yl)methyl]carbazole (Formula I: Ar=2,4-diaminopteridin-6-yl; W=$CH_2$; X=N; Z=chemical bond; m=n=0) is prepared similarly to N-(2,4-diaminopteridin-6-yl)methyl-N,N-diphenylamine as disclosed above by using carbazole (129 mg, 0.77 mmol), NaH (50 mg, 2.1 mmol), and 2,4-diamino-6-bromomethylpteridine hydrobromide (100 mg, 0.3 mmol). The product can be purified by chromatography.

EXAMPLE 15

N-[(2,4-Diaminopyrido[2,3-d]pyrimdin-6-yl)methyl]carbazole (Formula I: Ar=2,4-diaminopyrido[2,3-[pyrindin-6-yl; W=$CH_2$; X=N; Z=chemical bond; m=n=0) is prepared similarly to N-[(2,4-diaminopteridin-6-yl)methyl]N,N-diphenylamine as disclosed above by using carbazole (129 mg, 0.77 mmol), NaH (50 mg, 2.1 mmol), and 2,4-diamino-6-bromomethylpyrido[2,3-d]pyrimidine hydrobromide (100 mg, 0.3 mmol). The product can be purified by chromatography.

EXAMPLE 16

N-[(2,4-Diaminopyrido[3,2-d]pyrimidin-6-yl)methyl]carbazole (Formula I: Ar=2,4-diaminopyrido[2,3-d]pyrimidin-6-yl; W=$CH_2$; X=N; Z=chemical bond; m=n=0) is prepared similarly to N-[(2,4-diaminopteridin-6-yl)methyl]-N,N-diphenylamine as disclosed above by using carbazole (129 mg, 0.77 mmol), NaH (50 mg, 2.1 mmol), and 2,4-diamino-6-bromomethylpyrido[3,2-d]pyrimidine hydrobromide (100 mg, 0.3 mmol). The product can be purified by chromatography.

EXAMPLE 17

N-[(2,4-Diaminoquinazolin-6-yl)methyl]carbazole (Formula I: Ar=2,4-diaminoquinazolin-6-yl; W=$CH_2$; N=X; Z=chemical bond; m=n=0) is prepared similarly to N-[(2,4-diaminopteridin-6-yl)methyl]-N,N-diphenylamine as disclosed above by using carbazole (129 mg, 0.77 mmol), NaH (50 mg, 2.1 mmol), and 2,4-diamino-6-bromomethylquinaoline hydrobromide (100 mg, 0.3 mmol). The product can be purified by chromatography.

EXAMPLE 18

N-[(2,4-Diaminothieno[2,3-d]pyrimidin-5-yl)methyl]carbazole (Formula I: Ar=2,4-diaminothieno[2,3-d]

pyrimidin-5-yl; W=CH$_2$; X=N; Z=chemical bond; m=n=0) is prepared similarly to N-[(2,4-diaminothieno[2,3-d]pyrimidin-5-yl)methyl]-N,N-diphenylamine as disclosed in Example 11 above by using 2,4-diamino-5-methylthieno[2,3-d]pyrimidine (1.3 g, 7.2 mmol) in Step 1 and carbazole (129 mg, 0.8 mmol) in Step 3. The final product and its intermediates can be purified by chromatography.

EXAMPLE 19

N-[(2,4-Diaminofuro[2,3-d]pyrimidin-5-yl)methyl]carbazole (Formula I: Ar=2,4-diaminofuro[2,3-d]pyrimidin-5-yl; W=CH$_2$; X=N; Z=chemical bond; m=n=0) is prepared similarly to N-[(2,4-diaminofuro[2,3-d]pyrimidin-5-yl)methyl]-N,N-diphenylamine as disclosed in Example 11 above by using carbazole (129 mg, 0.8 mmol), NaH (50 mg, 2.1 mmol), and 2,4-diamino-5-chloromethylfuro[2,3-d]pyrimidine (60 mg, 0.3 mmol). The product can be purified by chromatography.

EXAMPLE 20

N-[(2,4-Diaminopyrimidin-6-yl)methyl]carbazole (Formula I: Ar=2,4-diaminopyrimidin-5-yl; W=CH$_2$; X=N; Z=chemical bond; m=n=0) is prepared similarly to N-[(2,4-diaminopteridin-6-yl)methyl]-N,N-diphenylamine as disclosed above by using carbazole (129 mg, 0.77 mmol), NaH (50 mg, 2.1 mmol), and 2,4-diamino-5-bromomethylpyrimidine hydrobromide (86 mg, 0.3 mmol). The product can be purified by chromatography.

EXAMPLE 21

N-[(2,4-Diaminopteridin-6-yl)methyl]-9,10-dihydroacridine (Formula I: Ar=2,4-diaminopteridin-6-yl; W=CH$_2$; N=X; Z=CH$_2$; m=n=0) is prepared similarly to N-[(2,4-diaminopteridin-6-yl)methyl]-N,N-diphenylamine as disclosed above by using 9,10 dihydroacridine (134 mg, 0.8 mmol), NaH (50 mg, 2.1 mmol), and 2,4-diamino-6-bromomethylpteridine hydrobromide (100 mg, 0.3 mmol). The product can be purified by chromatography.

EXAMPLE 22

N-[(2,4-Diaminopyrido[2,3-d]pyrimidin-6-yl)methyl]-9,10-dihydroacridine (Formula I: Ar=2,4-diaminopyrido[2,3-d]pyrimidin-6-yl; W=CH$_2$; X=N; Z=CH$_2$; m=n=0) is prepared similarly to N-[(2,4-diaminopteridin-6-yl)methyl]-N,N-diphenylamine as disclosed above by using 9,10-dihydroacridine (134 mg, 0.8 mmol), NaH (50 mg, 2.1 mmol), and 2,4-diamino-6-bromomethylpyrido[2,3-d]pyrimidine hydrobromide (100 mg, 0.3 mmol). The product can be purified by chromatography.

EXAMPLE 23

N-[(2,4-Diaminopyrido[3,2-d]pyrimidin-6-yl)methyl]-9,10-dihydroacridine (Formula I: Ar=2,4-diaminopyrido[3,2-d]pyrimidin-6-yl; W=CH$_2$; X=N; Z=CH$_2$; m=n=0) is prepared similarly to N-[(2,4-diaminopteridin-6-yl)methyl]-N,N-diphenylamine as disclosed above by using 9,10-dihydroacridine (134 mg, 0.8 mmol), NaH (50 mg, 2.1 mmol), and 2,4-diamino-6-bromomethylpyrido[3,2-d]pyrimidine hydrobromide (100 mg, 0.3 mmol). The product can be purified by chromatography.

EXAMPLE 24

N-[2,4-Diaminoquinazolin-6-yl)methyl]-9,10-dihydroacridine (Formula I: Ar=2,4-diaminoquinazolin-6-yl; W=CH$_2$; X=N; Z=CH$_2$; m=n=0) is prepared similarly to N-[(2,4-diaminopteridin-6-yl)methyl]-N,N-diphenylamine as disclosed above by using 9,10-dihydroacridine (134 mg, 0.8 mmol), NaH (50 mg, 2.1 mmol), and 2,4-diamino-6-bromomethylquinazoline hydrobromide (100 mg, 0.3 mmol). The product can be purified by chromatography.

EXAMPLE 25

N-[(2,4-Diaminothieno[2,3-d]pyrimidin-5-yl)methyl]-9,10-dihydroacridine (Formula I: Ar=2,4-diaminothieno[2,3-d]pyrimidi-5-yl; W=CH$_2$; X=N; Z=CH$_2$; m=n=0) is prepared similarly to N-[(2,4-diaminothieno[2,3-d]pyrimidin-5-yl)methyl]-N,N-diphenylamine as disclosed in Example 11 above by using 2,4-diamino-5-methylthieno[2,3-d]pyrimidine (1.3 g, 7.4 mmol) in Step 1 and 9,10-dihydroacridine (134 mg, 0.8 mmol) in Step 3. The final product and its intermediates can b purified by chromatography.

EXAMPLE 26

N-[(2,4-Diaminofuro[2,3-d]pyrimidin-5-yl)methyl]-9,10-dihydroacridine (Formula I: Ar=2,4-diaminofuro[2,3-d]pyrimidin-5-yl; W=CH$_2$; X=N; Z=CH$_2$; m=n=0) is prepared similarly to N-[(2,4-diaminofuro[2,3-d]pyrimidin-5-yl)methyl]-N,N-diphenylamine as disclosed in Example 11 above by using 9,10-dihydroacridine (134 mg, 0.8 mmol), NaH (50 mg, 2.1 mmol), and 2,4-diamino-5-chloromethylfuro[2,3-d]pyrimidine (60 mg, 0.3 mmol). The product can be purified by chromatography.

EXAMPLE 27

N-[(2,4-Diaminopyrimidin-6-yl)methyl]-9,10-dihydroacridine (Formula I: Ar=2,4-diaminopyrimidin-5-yl; W=CH$_2$; X=N; Z=CH$_2$; m=n=0) is prepared similarly to N-[(2,4-diaminopteridin-6-yl)methyl]-N,N-diphenylamine as disclosed above by using 9,10-dihydroacridine (134 mg, 0.8 mmol), NaH (50 mg, 2.1 mmol), and 2,4-diamino-5-bromomethylpyrimidine hydrobromide (86 mg, 0.3 mmol). The product can be purified by chromatography.

EXAMPLE 28

N-[(2,4-Diaminopteridin-6-yl)methyl]phenoxazine (Formula I: Ar=2,4-diaminopteridin-6-yl; W=CH$_2$; X=N; Z=O; m=n=0) is prepared similarly to N-[(2,4-diaminopteridin-6-yl)methyl]-N,N-diphenylamine as disclosed above by using phenoxazine (146 mg, 0.8 mmol), NaH (50 mg, 2.1 mmol), and 2,4-diamino-6-bromomethylpteridine hydrobromide (100 mg, 0.3 mmol). The final product can be purified by chromatography.

EXAMPLE 29

9-[(2,4-Diaminopyrido[2,3-d]pyrimidin-6-yl)methyl]phenoxazine (Formula I: Ar=2,4-diaminopyrido[2,3-d]pyrimidin-6-yl; W=CH$_2$; X=N; Z=O; m=n=0) is prepared similarly to N-[(2,4-diaminopteridin-6-yl)methyl]-N,N-diphenylamine as disclosed above by using phenoxazine (146 mg, 0.8 mmol), NaH (50 mg, 2.1 mmol), and 2,4-diamino-6-bromomethylpyrido[2,3-d]pyrimidine hydrobromide (100 mg, 0.3 mmol). The product can be purified by chromatography.

EXAMPLE 30

9-[(2,4-Diaminopyrido[3,2-d]pyrimidin-6-yl)methyl]phenoxazine (Formula I: Ar=2,4-diaminopyrido[3,2-d]

pyrimidin-6-yl; W=CH$_2$; X=N; Z=O; m=n=0) is prepared similarly to N-[(2,4-diaminopteridin-6-yl)methyl]-N,N-diphenylamine as disclosed above by using phenoxazine (146 mg, 0.8 mmol), NaH (50 mg, 2.1 mmol), and 2,4-diamino-6-bromomethylpyrido[3,2-d]pyrimidine hydrobromide (100 mg, 0.3 mmol). The product can be purified by chromatography.

EXAMPLE 31

9-[(2,4-Diaminoquinazolin-6-yl)methyl]phenoxazine (Formula I: Ar=2,4-diaminoquinazolin-6-yl; W=CH$_2$; X=N; Z=O; m=n=0) is prepared similarly to N-[(2,4-diaminopteridin-6-yl)methyl]-N,N-diphenylamine as disclosed above by using phenoxazine (146 mg, 0.8 mmol), NaH (50 mg, 2.1 mmol), and 2,4-diamino-6-bromomethylquinazoline hydrobromide (100 mg, 0.3 mmol). The product can be purified by chromatography.

EXAMPLE 32

9-[(2,4-Diaminothieno[2,3-d]pyrimidin-5-yl)methyl]phenoxazine (Formula I: Ar=2,4-diaminothieno[2,3-d]pyrimidin-5-yl; W=CH$_2$; X=N; Z=O; m=n=0) is prepared similarly to N-[(2,4-diaminothieno[2,3-d]pyrimidin-5-yl)methyl]-N,N-diphenylamine as disclosed in Example 11 above by using 2,4-diamino-5-methylthieno[2,3-d]pyrimidine (1.3 g, 7.4 mmol) in Step 1 and phenoxazine (146 mg, 0.8 mmol) in Step 3. The final product and its intermediates can be purified by chromatography.

EXAMPLE 33

9-[(2,4-Diaminofuro[2,3-d]pyrimidin-5-yl)methyl]phenoxazine (Formula I: Ar=2,4-diaminofuro[2,3-d]pyrimidin-5-yl; W=CH$_2$; X=N; Z=O; m=n=0) is prepared similarly to N-[(2,4-diaminothieno[2,3-d]pyrimidin-5-yl)methyl]-N,N-diphenylamine as disclosed in Example 11 above by using phenoxazine (146 mg, 0.8 mmol), NaH (50 mg, 2.1 mmol), and 2,4-diamino-5-chloromethylfuro[2,3-d]pyrimidine (60 mg, 0.3 mmol). The product can be purified by chromatography.

EXAMPLE 34

9-[(2,4-Diaminopyrimidin-6-yl)methyl]phenoxazine (Formula I: Ar=2,4-diaminopyrimidin-5-yl; W=CH$_2$; X=N; Z=O; m=n=0) is prepared similarly to N-[(2,4-diaminopteridin-6-yl)methyl]-N,N-diphenylamine as disclosed above by using phenoxazine (146 mg, 0.8 mmol), NaH (50 mg, 2.1 mmol), and 2,4-diamino-5-bromomethylpyridine hydrobromide (86 mg, 0.3 mmol). The product can be purified by chromatography.

EXAMPLE 35

N-[(2,4-Diaminopteridin-6-yl)methyl]phenothiazine (Formula I: Ar=2,4-diaminopteridin-6-yl; W=CH$_2$ X=N; Z=S; m=n=0) is prepared similarly to N-[(2,4-diaminopteridin-6-yl)methyl]-N,N-diphenylamine as disclosed above by using phenothiazine (159 mg, 0.8 mmol), NaH (50 mg, 2.1 mmol), and 2,4-diamino-6-bromomethylpteridine hydrobromide (100 mg, 0.3 mmol). The product can be purified by chromatography.

EXAMPLE 36

9-[(2,4-Diaminopyrido[2,3-d]pyrimidin-6-yl)methyl]phenothiazine (Formula I: Ar=2,4-diaminopyrido[2,3-d]pyrimidin-6-yl; W=CH$_2$; X=N; Z=S; m=n=0) is prepared similarly to N-[(2,4-diaminopteridin-6-yl)methyl]-N,N-diphenylamine as disclosed above by starting from phenothiazine (159 mg, 0.8 mmol), NaH (50 mg, 2.1 mmol), and 2,4-diamino-6-bromomethylpyrido[2,3-d]pyrimidine hydrobromide (100 mg, 0.3 mmol). The product can be purified by chromatography.

EXAMPLE 37

9-[(2,4-Diaminopyrido[3,2-d]pyrimidin-6-yl)methyl]phenothiazine (Formula I: Ar=2,4-diaminopyrido[3,2-d]pyrimidin-6-yl; W=CH$_2$; X=N; Z=S; m=n=0) is prepared similarly to N-[(2,4-diaminopteridin-6-yl)methyl]-N,N-diphenylamine as disclosed above by using phenothiazine (159 mg, 0.8 mmol), NaH (50 mg, 2.1 mmol), and 2,4-diamino-6-bromomethylpyrido[3,2-d]pyrimidine hydrobromide (100 mg, 0.3 mmol). The product can be purified by chromatography.

EXAMPLE 38

9-[(2,4-Diaminoquinazolin-6-yl)methyl]phenothiazine (Formula I: Ar=2,4-diaminoquinazolin-6-yl; W=CH$_2$; X=N; Z=S; m=n=0) is prepared similarly to N-[(2,4-diaminopteridin-6-yl)methyl]-N,N-diphenylamine as disclosed above by using phenothiazine (159 mg, 0.8 mmol), NaH (50 mg, 2.1 mmol), and 2,4-diamino-6-bromomethylquinazoline hydrobromide (100 mg, 0.3 mmol). The product can be purified by chromatography.

EXAMPLE 39

9-[(2,4-Diaminothieno[2,3-d]pyrimidin-5-yl)methyl]phenothiazine (Formula I: Ar=2,4-diaminothieno[2,3-d]pyrimidin-5-yl; W=CH$_2$; X=N; Z=S; m=n=0) is prepared similarly to N-[(2,4-diaminothieno[2,3-d]pyrimidin-5-yl)methyl]-N,N-diphenylamine as disclosed in Example 11 above by using 2,4-diamino-5-methylthieno[2,3-d]pyrimidine (1.3 g, 7.4 mmol) in Step 1 and phenothiazine (159 mg, 0.8 mmol) in Step 3. The final product and its intermediates can be purified by chromatography.

EXAMPLE 40

9-[(2,4-Diaminofuro[2,3-d]pyrimidin-5-yl)methyl]phenothiazine (Formula I: Ar=2,4-diaminofuro[2,3-d]pyrimidin-5-yl; W=CH$_2$; X=N; Z=S; m=n=0) is prepared similarly to N-[(2,4-diaminofuro[2,3-d]pyrimidin-5-yl)methyl]-N,N-diphenylamine as disclosed above by using phenothiazine (159 mg, 0.8 mmol), NaH (50 mg, 2.1 mmol), and 2,4-diamino-5-chloromethylfuro[2,3-d]pyrimidine (60 mg, 0.3 mmol). The product can be purified by chromatography.

EXAMPLE 41

9-[(2,4-Diaminopyrimidin-5-yl)methyl]phenothiazine (Formula I: Ar=2,4-diaminopyrimidin-5-yl; W=CH$_2$; X=N; Z=S; m=n=0) is prepared similarly to N-[(2,4-diaminopteridin-6-yl)methyl]-N,N-diphenylamine as disclosed above by using phenothiazine (159 mg, 0.8 mmol), NaH (50 mg, 2.1 mmol), and 2,4-diamino-5-bromomethylpyridine hydrobromide (86 mg, 0.3 mmol). The product can be purified by chromatography.

EXAMPLE 42

N-[(2,4-Diaminopteridin-6-yl)methyl]-9,10-dihydrodibenz[b,f]azepine (Formula I: Ar=2,4-diaminopteridiin-6-yl; W=CH$_2$; X=N; Z=CH$_2$CH$_2$; m=n=0)

is prepared similarly to N-[(2,4-diaminopteridin-6-yl)methyl]-N,N-diphenylamine as disclosed above by using 9,10-dihydrodibenz[b,f]azepine (158 mg, 0.8 mmol), NaH (50 mg, 2.1 mmol), and 2,4-diamino-6-bromomethylpteridine hydrobromide (100 mg, 0.3 mmol). The product can be purified by chromatography.

EXAMPLE 43

9-[(2,4-Diaminopyrido[2,3-d]pyrimidin-6-yl)methyl]-9,10-dihydrodibenz-[b,f]azepine (Formula I: Ar=2,4-diaminopyrido[2,3-d]pyrimidin-6-yl; W=CH$_2$; X=N; Z=CH$_2$=CH$_2$; m=n=0) is prepared similarly to N-[(2,4-diaminopteridin-6-yl)methyl]-N,N-diphenylamine as disclosed above by using 9,10-dihydrodibenz[b,f]azepine (158 mg, 0.8 mmol), NaH (50 mg, 2.1 mmol) and 2,4-diamino-6-bromomethylpyrido[2,3-d]pyrimidine hydrobromide (100 mg, 0.3 mmol). The product can be purified by chromatography.

EXAMPLE 44

9-[(2,4-Diaminopyrido[3,2-d]pyrimidin-6-yl)methyl]-9,10-dihydrodibenz-[b,f]azepine (Formula I: Ar=2,4-diaminopyrido[3,2-d]pyrimidin-6-yl; W=CH$_2$; X=N; Z=CH$_2$CH$_2$; m=n=0) is prepared similarly to N-[(2,4-diaminopteridin-6-yl)methyl]-N,N-diphenylamine as disclosed above by using 9,10-dihydrodibenz[b,f]azepine (158 mg, 0.8 mmol), NaH (50 mg, 2.1 mmol), and 2,4-diamino-6-bromomethylpyrido[3,2-d]pyrimidine hydrobromide (100 mg, 0.3 mmol). The product can be purified by chromatography.

EXAMPLE 45

9-[(2,4-Diaminoquinazolin-6-yl)methyl]-9,10-dihydrodibenz[b,f]azepine (Formula I: Ar=2,4-diaminoquinazolin-6-yl; W=CH$_2$; X=N; Z=CH$_2$CH$_2$; m=n=0) is prepared similarly to N-[(2,4-diaminopteridin-6-yl)methyl]-N,N-diphenylamine as disclosed above by using 9,10-dihydrodibenz[b,f]azepine (158 mg, 0.8 mmol), NaH (50 mg, 2.1 mmol), and 2,4-diamino-6-bromomethylquinazoline hydrobromide (100 mg, 0.3 mmol). The product can be purified by chromatography.

EXAMPLE 46

9-[(2,4-Diaminothieno[2,3-d]pyrimidin-5-yl)methyl]-9,10-dihydrodibenz-[b,f]azepine (Formula I: Ar=2,4-diaminohieno[2,3-d]pyrimidi-5-yl; W=CH$_2$; X=N; Z=CH$_2$CH$_2$; m=n=0) is prepared similarly to N-[(2,4-diaminothieno[2,3-d]pyrimidin-5-yl)methyl]-N,N-diphenylamine as disclosed in Example 11 above, by using 2,4-diamino-5-methylthieno[2,3-d]pyrimidine (1.3 g, 7.4 mmol) in Step 1 and 9,10-dihydrodibenz[b,f]azepine (158 mg, 0.8 mmol) in Step 3. The final product and its intermediates chromatography.

EXAMPLE 47

9-[(2,4-Diaminofuro[2,3-d]pyrimidin-5-yl)methyl]-9,10-dihydrodibenz-[b,f]azepine (Formula I: Ar=2,4-diaminofuro[2,3-d]pyrimidin-5-yl; W=CH$_2$; X=N; Z=CH$_2$CH$_2$; m=n=0) is prepared similarly to N-[(2,4-diaminofuro[2,3-d]pyrimidin-5-yl)methyl]-N,N-diphenylamine as disclosed above by using 9,10-dihydrodibenz[b,f]azepine (158 mg, 0.8 mmol), sodium hydride (50 mg, 2.1 mmol), and 2,4-diamino-5-chloromethylfuro[2,3-d]pyrimidine (60 mg, 0.3 mmol). The product can be purified by chromatography.

EXAMPLE 48

9-[(2,4-Diaminopyrimidin-5-yl)methyl]-9,10-dihydrodibenz[b,f]azepine (Formula I: Ar=2,4-diaminopyrimidin-5-yl; W=CH$_2$; X=N; Z=CH=CH; m=n=0) is prepared similarly to N-[(2,4-diaminopteridin-6-yl)methyl]-N,N-diphenylamine as disclosed above by using 9,10-dihydrodibenz[b,f]azepine (158 mg, 0.8 mmol), NaH (50 mg, 2.1 mmol), and 2,4-diamino-5-bromomethylpyrimidine hydrobromide (86 mg, 0.3 mmol). The product can be purified by chromatography.

EXAMPLE 49

N-[(2,4-Diaminopteridin-6-yl)methyl]dibenz[b,f]azepine (Formula I: Ar=2,4-diaminopteridin-6-yl; W=CH$_2$; X=N; Z=CH=CH; m=n=0) is prepared similarly to N-[(2,4-diaminopteridin-6-yl)methyl]-N,N-diphenylamine as disclosed above, by using dibenz[b,f]azepine (154 mg, 0.8 mmol), NaH (50 mg, 2.1 mmol), and 2,4-diamino-6-bromomethylpteridine hydrobromide (100 mg, 0.3 mmol). The product can be purified by chromatography.

EXAMPLE 50

9-[(2,4-Diaminopyrido[2,3-d]pyrimidin-6-yl)methyl]dibenz[b,f]azepine (Formula I: Ar=2,4-diaminopyrido[2,3-d]pyrimidin-6-yl; W=CH$_2$; X=N; Z=CH=CH; m=n=0) is prepared similarly to N-[(2,4-diaminopteridin-6-yl)methyl]-N,N-diphenylamine as disclosed above by using dibenz[b,f]azepine (154 mg, 0.8 mmol), NaH (50 mg, 2.1 mmol), and 2,4-diamino-6-bromomethylpyrido[2,3-d]pyrimidine hydrobromide (100 mg, 0.3 mmol). The product can be purified by chromatography.

EXAMPLE 51

9-[(2,4-Diaminopyrido[3,2-d]pyrimidin-6-yl)methyl]dibenz[b,f]azepine (Formula I: Ar=2,4-diaminopyrido[3,2-d]pyrimidin-6-yl; W=CH$_2$; X=N; Z=CH=CH; m=n=0) is prepared similarly to N-[(2,4-diaminopteridin-6-yl)methyl]-N,N-diphenylamine as disclosed above by using dibenz[b,f]azepine (154 mg, 0.8 mmol), NaH (50 mg, 2.1 mmol), and 2,4-diamino-6-bromomethylpyrido[3,2-d]pyrimidine hydrobromide (100 mg, 0.3 mmol). The product can be purified by chromatography.

EXAMPLE 52

9-[(2,4-Diaminoquinazolin-6-yl)methyl]dibenz[b,f]azepine (Formula I: Ar=2,4-diaminoquinazolin-6-yl; W=CH$_2$; X=N; Z=CH=CH; m=n=0) is prepared similarly to N-[(2,4-diaminopteridin-6-yl)methyl]-N,N-diphenylamine as disclosed above by using dibenz[b,f]azepine (154 mg, 0.8 mmol), NaH (50 mg, 2.1 mmol), and 2,4-diamino-6-bromomethylquinazoline hydrobromide (100 mg, 0.3 mmol). The product can be purified by chromatography.

EXAMPLE 53

9-[(2,4-Diaminothieno[2,3-d]pyrimidin-5-yl)methyl]dibenz[b,f]azepine (Formula I: Ar=2,4-diaminothieno[2,3-d]pyrimidin-5-yl; W=CH$_2$; X=N; Z=CH=CH; m=n=0) is prepared similarly to N-[(2,4-diaminothieno[2,3-d]pyrimidin-5-yl)methyl]-N,N-diphenylamine as disclosed above by using 2,4-diamino-5-methylthieno[2,3-d]pyrimidine (1.3 g, 7.4 mmol) in Step 1 and dibenz[b,f]azepine (154 mg, 0.8 mmol) in Step 3. The final product and its intermediates can be purified by chromatography.

EXAMPLE 54

9-[(2,4-Diaminofuro[2,3-d]pyrimidin-5-yl)methyl]benz[b,f]azepine (Formula I: Ar=2,4-diaminofuro[2,3-d]

pyrimidin-5-yl; W=CH$_2$; X=N; Z=CH═H; m=n=0) is prepared similarly to N-[(2,4-diaminofuro[2,3-d]pyrimidin-5-yl)methyl]-N,N-diphenylamine as disclosed above by using dibenz[b,f]azepine (154 mg, 0.8 mmol), NaH (50 mg, 2.1 mmol), and 2,4-diamino-5-chloromethylfuro[2,3-d]pyrimidine (60 mg, 0.3 mmol). The product can be purified by chromatography.

EXAMPLE 55

9-[(2,4-Diaminopyrimidin-6-yl)methyl]dibenz[b,f]azepine (Formula I: Ar=2,4-diaminopyrimidin-5-yl; W=CH$_2$; X=N; Z=CH═CH; m=n=0) is prepared similarly to N-[(2,4-diaminopteridin-6-yl)methyl]-N,N-diphenylamine as disclosed above by using dibenz[b,f]azepine (154 mg, 0.8 mmol), NaH (50 mg, 2.1 mmol), and 2,4-diamino-5-bromomethylpyrimidine hydrobromide (86 mg, 0.3 mmol). The product can be purified by chromatography.

EXAMPLE 56

N-(2,4-Diaminopyrido[2,3-d]pyrimidin-6-yl)benzhydrylamine (Formula I: Ar=2,4-diaminopyrido[2,3-d]pyrimidin-6-yl; W=NH; X=CH; Z=non-linked hydrogens on each phenyl group; m=n=0).

A solution of benzhydrylamine (366 mg, 2.0 mmol) and 2,4,6-triaminopyrido[2,3-d]pyrimidine (350 mg, 2.0 mmol) in a mixture of DMF (40 mL) and glacial AcOH (4 mL) is treated with BH$_3$.Et$_3$N (75 mg, 6.6 mmol), and the mixture is stirred at room temperature overnight, then diluted with H$_2$O (20 mL) to decompose any unreacted reducing agent. The solvents are evaporated under reduced pressure, and the residue is purified on a silica gel column using 5–15% CHCl$_3$ in MeOH as the eluent. Pooling and evaporation of appropriate fractions yields the title compound, N-(2,4-diaminopyrido[2,3-d]pyrimidin-6-yl)benzhydrylamine.

EXAMPLE 57

N-[(2,4-Diaminoquinazolin-6-yl)amino]benzhydrylamine (Formula I: Ar=2,4-diaminoquinazolin-6-yl; W=NH; X=CH; Z=non-linked hydrogens on each phenyl group; m=n=0) is prepared similarly to N-[(2,4-diaminopyrido[2,3-d]pyrimidin-6-yl)amino]benzhydrylamine as disclosed above by using benzhydrylamine (366 mg, 2.0 mmol), 2,4,6-triaminoquinazoline (350 mg, 2.0 mmol), and BH$_3$.Et$_3$N (75 mg, 6.6 mmol). The product can be purified by chromatography.

EXAMPLE 58

N-[(2,4-Diaminopyrimidin-5-yl)methyl]benzhydrylamine (Formula I: Ar=2,4-diaminopyrimidin-5-yl); W=CH$_2$NH; X=CH; Z=non-linked hydrogens on each phenyl group; m=n=0) is prepared similarly to N-(2,4-diaminopyrido[2,3-d]pyrimidin-6-yl)amino]benzhydrylamine as disclosed above by using benzhydrylamine (366 mg, 2.0 mmol), 2,4-diamino-5-aminomethylpyrimidine (278 mg, 2.0 mmol), mg, 2 mmol), and BH$_3$.Et$_3$N (75 mg, 6.6 mmol). The product can be purified by chromatography.

EXAMPLE 59

N-[(2,4-Diaminopyrimidin-5-yl)ethyl]benzhydrylamine (Formula I: Ar=2,4-diaminopyrimidin-5-yl; W=CH$_2$CH$_2$NH; X=CH; Z=non-linked hydrogens on each phenyl group; m=n=0) is prepared similarly to N-(2,4-diaminopyrido[2,3-d]pyrimidin-6-yl)amino]

benzhydrylamine as disclosed above by using benzhydrylamine (366 mg, 2.0 mmol), 2,4-diamino-5-(2-aminoethyl)pyrimidine (306 mg, 2.0 mmol), mg, 2.0 mmol), and BH$_3$.Et$_3$N (75 mg, 6.6 mmol). The product can be purified by chromatography.

EXAMPLE 60

9-[N-(2,4-Diaminopyrido[2,3-d]pyrimidin-6-yl)amino]fluorene (Formula I: Ar=2,4-diaminopyrido[2,3-d]pyrimidin-6-yl; W=NH; X=CH; Z=chemical bond; m=n=0) is prepared similarly to N-(2,4-diaminopyrido[2,3-d]pyrimidin-6-yl)amino]benzhydrylamine as disclosed above by using fluorenone (360 mg, 2.0 mmol), 2,4,6-triaminopyrido[2,3-d]pyrimidine (350 mmol), mg, 2.0 mmol), and BH$_3$.Et$_3$N (75 mg, 6.6 mmol). The product can be purified by chromatography.

EXAMPLE 61

9-[N-(2,4-Diaminoquinazolin-6-yl)amino]fluorene (Formula I: Ar=2,4-diaminoquinazolin-6-yl; W=NH; Z=CH; Z=chemical bond; m=n=0) is prepared similarly to N-(2,4-diaminopyrido[3,2-d]diamino]fluorene as disclosed above by using fluorenone (360 mg, 2.0 mmol), 2,4,6-triaminoquinazoline (350 mg, 2.0 mmol), and BH$_3$.Et$_3$N (75 mg, 6.6 mmol). The product can be purified by chromatography.

EXAMPLE 62

9-[N-(2,4-Diaminopyrimidin-5-yl)methylamino]fluorene (Formula I: Ar=2,4-diaminopyrimidin-5-yl; W=CH$_2$NH is prepared similarly to N-(2,4-diaminopyrido-[2,3-d]pyrimidin-6-yl)amino]fluorene as disclosed above by using fluorenone (360 mg, 2.0 mmol), 2,4-diamino-5-aminomethylpyrimidine (278 mg, 2.0 mmol), and BH$_3$.Et$_3$N (75 mg, 6.6 mmol). The product can be purified by chromatography.

EXAMPLE 63

9-[N-[2-(2,4-Diaminopyrimidin-5-yl)ethyl]amino]fluorene (Formula I: Ar=2,4-diaminopyrimidin-5-yl); W=CH$_2$CH$_2$NH; X=CH; Z=chemical bond; m=n=0) is prepared similarly to N-(2,4-diaminopyrido[2,3-d]pyrimidin-6-yl)amino]fluorene as disclosed above by using fluorenone (360 mg, 2.0 mmol), 2,4-diamino-5-2-aminoethyl)pyrimidine (306 mg, 2.0 mmol), and BH$_3$.Et$_3$N (75 mg, 6.6 mmol). The product can be purified by chromatography.

EXAMPLE 64

5-[N-(2,4-Diaminopyrido[2,3-d]pyrimidin-6-yl)amino]-5H-10,11-dihydro-dibenzo[a,d]-cycloheptene (Formula I: Ar=2,4-diaminopyrido[2,3-d]pyrimidin-6-yl; W=NH; X=CH; Z=CH$_2$CH$_2$; m=n=0) is prepared similarly to N-(2, 4-diaminopyrido-[2,3-d]pyrimidin-6-yl)amino]fluorene as disclosed above by using 5H-dibenzo[a,d]cycloheptene-5-one (416 mg, 2.0 mmol), 2,4,6-triaminopyrido[2,3-d]pyrimidine (350 mg, 2.0 mmol), and BH$_3$.Et$_3$N (75 mg, 6.6 mmol). The product can be purified by chromatography.

EXAMPLE 65

5-[N-(2,4-Diaminoquinazolin-6-yl)amino]-5H-10,11-dihydrodibenzo[a,d]-cycloheptene (Formula I: Ar=2,4-diaminoquinazolin-6-yl; W=NH; X=CH; Z=CH$_2$CH$_2$; m=n=0) is prepared similarly to N-(2,4-diaminopyrido[2,3-diamino]fluorene as disclosed above by using 5H-dibenzo

[a,d]cycloheptane-5-one (416 mg, 2.0 mmol), 2,4,6-triaminoquinazoline (350 mg, 2.0 mmol), and $BH_3.Et_3N$ (75 mg, 6.6 mmol). The product can be purified by chromatography.

EXAMPLE 66

5-[N-(2,4-Diaminopyrimidin-5-yl)methylamino]-5H-10,11-dihydro-dibenzo[a,d]heptene (Formula I: Ar=2,4-diaminopyrimidin-5-yl; W=$CH_2NH$; Z=$CH_2CH_2$; m=n=0) is prepared similarly to N-(2,4-diaminopyrido[2,3-d]pyrimidin-6-yl)amino]fluorene as disclosed above by using 5H-dibenzo[a,d]cycloheptan-5-one (416 mg, 2.0 mmol), 2,4-diamino-5-aminomethylpyrimidine (278 mg, 2.0 mmol), and $BH_3.Et_3N$ (75 mg, 6.6 mmol). The product can be purified by chromatography.

EXAMPLE 67

5-[N-[2-(2,4-Diaminopyrimidin-5-yl)ethyl]amino]5H-10,11-dihydro-dibenzo[a,d]cycloheptene (Formula I: Ar=2,4-diaminopyrimidin-5-yl; W=$CH_2CH_2NH$; X=CH; Z=CH=CH; m=n=0) is prepared similarly to N-(2,4-diaminopyrido[2,3-d]pyrimidin-6-yl)amino]fluorene as disclosed above by using 5H-dibenzo[a,d]cycloheptan-5-one (416 mg, 2.0 mmol), 2,4-diamino-5-(2-aminoethyl)pyrimidine (306 mg, 2.0 mmol), and $BH_3.Et_3N$ (75 mg, 6.6 mmol). The product can be purified by chromatography.

EXAMPLE 68

5-[N-(2,4-Diamino]-5H-dibenzo[a,d]-cycloheptene (Formula I: Ar=2,4-diaminopyrido[2,3-d]pyrimidin-6-yl; W=NH; X=CH; Z=CH=CH; m=n=0) is prepared similarly to N-(2,4-diaminopyrido[2,3-d]pyrimidin-6-yl)amino]fluorene as disclosed above by using 5H-dibenzo[a,d]cyclohepten-5-one (412 mg, 2.0 mmol), 2,4,6-triaminopyrido[2,3-d]pyrimidine (350 mg, 2.0 mmol), and $BH_3.Et_3N$ (75 mg, 6.6 mmol). The product can be purified by chromatography.

EXAMPLE 69

5-[N-(2,4-Diaminoquinazolin-6-yl)amino]-5H-dibenzo[a,d]cycloheptene (Formula I: Ar=2,4-diaminoquinazolin-6-yl; W=NH; X=CH; Z=CH=CH; m=n=0) is prepared similarly to N-(2,4-diaminopyrido[2,3-d]pyrimidin-6-yl)amino]fluorene as disclosed above by using 5H-dibenzo[a,d]cycloheptan-5-one (412 mg, 2.0 mmol), 2,4,6-triaminoquinazoline (350 mg, 2.0 mmol), and $BH_3.Et_3N$ (75 mg, 6.6 mmol). The product can be purified by chromatography.

EXAMPLE 70

5-[N-(2,4-Diaminopyrimidin-5-yl)methylamino]-5H-dibenzo[a,d]heptene (Formula I: Ar=2,4-diaminopyrimidin-5-yl; W=$CH_2NH$; X=CH; Z=chemical bond; m=n=0) is prepared similarly to N-(2,4-diaminopyrido[2,3-d]pyrimidin-6-yl)amino]fluorene as disclosed above by using 5H-dibenzo[a,d]cyclohept an-5-one (412 mg, 2.0 mmol), 2,4-diamino-5-aminomethylpyrimidine (278 mg, 2.0 mmol). The product can be purified by chromatography.

EXAMPLE 71

5-[N-[2-(2,4-Diaminopyrimidin-5-yl)ethyl]amino]-5H-dibenzo[a,d]heptene (Formula I: Ar=2,4-diaminopyrimidin-5-yl); W=$CH_2CH_2NH$; X=CH=CH; m=n=0) is prepared similarly to N-(2,4-diaminopyrido[2,3-d]pyrimidin-6-yl)amino]fluorene as disclosed above by using 5H-dibenzo[a,d]cyclohept an-5-one (412 mg, 2.0 mmol), 2,4-diamino-5-2-aminoethyl)pyrimidine (306 mg, 2.0 mmol), and $BH_3.Et_3N$ (75 mg, 6.6 mmol). The product can be purified by chromatography.

EXAMPLE 72

Dihydrofolate reductase inhibition

Compounds of the invention were tested for inhibition of dihydrofolate reductase (DHFR) from rat liver, *Pneumocystis carinii* and *Toxoplasmosis gondii*. $IC_{50}$ values were determined, which is the concentration (:M) of a compound required to inhibit the dihydrofolate reductase activity by 50%. Selectivity ratios are also set forth in the table. The DHFR inhibition assay was conducted by the procedures disclosed in Broughton, M. C. et al., *Antimicrob. Agents Chemother.*, 1991, 35: 1348–1355; Chio, L. C. et al., *Antimicrob. Agents Chemother.*, 1993, 37: 1914–1923. Results are set forth in Table 1 below, with the tested compound identified by reference to the structural formula set forth at the top of the table.

TABLE 1

Inhibition of *Pneumocystis carinii*, *Toxoplasma gondii*, and rat liver dihydrofolate reductase by compounds of the invention.

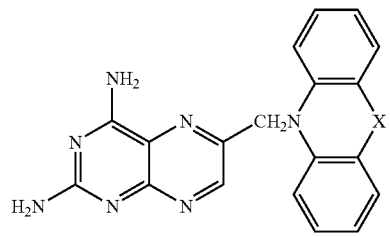

| | | DHFR inhibition ($IC_{50}$ μM)[c] | | | selectivity ratio | |
| | | | | | rat liver/ | rat liver/ |
| cmpd | X | P.carinii | T.gondii | rat liver | P.carinii | T. gondii liver |
|---|---|---|---|---|---|---|
| 1 | a | 4.9 | 1.3 | 2.8 | 0.57 | 2.2 |
| 2 | b | 0.10 | 0.055 | 0.012 | 0.55 | 0.022 |

TABLE 1-continued

Inhibition of *Pneumocystis carinii*, *Toxoplasma gondii*, and rat liver dihydrofolate reductase by compounds of the invention.

|  |  |  | DHFR inhibition (IC$_{50}$ µM)[c] | | | selectivity ratio | |
|---|---|---|---|---|---|---|---|
|  |  |  |  |  |  | rat liver/ | rat liver/ |
| cmpd | X |  | P.carinii | T.gondii | rat liver | P.carinii | T. gondii liver |
| 3 | CH$_2$ |  | 0.042 | 0.029 | 0.027 | 0.64 | 0.93 |
| 4 | O |  | 3.4 | 2.2 | 13 | 3.8 | 5.9 |
| 5 | S |  | 0.12 | 0.11 | 0.20 | 1.7 | 1.8 |
| 6[c] | CH$_2$CH$_2$ | expt 1 | 1.7 | 0.89 | 4.4 |  |  |
|  |  | expt 2 | 1.0 | 0.93 | 2.7 |  |  |
|  |  | mean | 1.4 | 0.91 | 5.1 | 3.6 | 5.6 |
| 7[c] | CH=CH | expt 1 | 0.24 | 0.010 | 2.1 |  |  |
|  |  | expt 2 | 0.18 | 0.041 | 9.3 |  |  |
|  |  | expt 3 |  | 0.084 | 4.4 |  |  |
|  |  | mean | 0.21 | 0.045 | 5.3 | 25 | 118 |

[a]No bridge between the phenyl rings (i.e. X is non-linked hydrogens)
[b]Direct bridge between the phenyl rings (i.e. X is a chemical bond)
[c]Replicate assays performed on different days

EXAMPLE 73

Additional data of N-[2,4-diaminopteridin-6-yl) methyldibenz[b,f]azepine

It was also found that N-[2,4-diaminopteridin-6-yl) methyldibenz[b,f]azepine inhibited the proliferation of *T. gondii* cells in culture as measured by a standard assay based on [$^3$H]uracil incorporation into the acid-insoluble fraction. The assay protocol is disclosed in Chio, L. C. et al., *Antimicrob. Agents Chemother.*, 1993, 37: 1914–1923. Incorporation relative to untreated controls was inhibited by 90% at a concentration of N-[2,4-diaminopteridin-6-yl) methyldibenz[b,f]azepine of 1 micromolar and the IC$_{50}$ was about 0.3 micromolar. A typical IC$_{50}$ for current antixoplasmosis clinic agent pyrimethamine in this assay is 0.5–0.8 micromolar. It thus appears that N-[2,4-diaminopteridin-6-yl)methyldibenz[b,f]azepine is at least as active as pyrimethamine in this assay.

The ratio IC$_{50}$(uracil incorporation)/IC$_{50}$ (DHFR inhibition) can indicate the efficiently of drug uptake by a parasite. In the case of the clinical agent pyrimethamine, this ratio is about 1.7. In the case of N-[2,4-diaminopteridin-6-yl)methyldibenz[b,f]azepine, whose IC$_{50}$ (DHFR inhibition) is 0.045 micromolar and whose IC$_{50}$ (uracil incorporation) is about 0.3 micromolar, the ratio calculated from these data is 6.7. That indicates that the uptake of N-[2,4-diaminopteridin-6-yl)methyldibenz[b,f]azepine is about four times more efficient than that of pyrimethamine.

N-[2,4-diaminopteridin-6-yl)methyldibenz[b,f]azepine is also active against intact *P. carinii* cells as measured by a different assay based on incorporation of [$^3$H]para-aminobenzoic acid (PABA) into the total cellular folate pool of freshly harvested cells from a rat. The assay protocol that was employed is described in Kovacs, J. A., et al., *J. Infect. Dis.*, 1989, 160: 312–320; and Chio, L. C. et al., *Antimicrob. Agents Chemother.*, 1993, 37: 1914–1923. This assay can be used as measure of cell viability after drug treatment, and relies on the fact that *P. carinii* do not take up exogenous folates but can make their own folates de novo from PABA. After 5 hours of treatment with 17.6 micromolar N-[2,4-diaminopteridin-6-yl)methyldibenz[b,f]azepine there was about a 60% decrease in uptake of [$^3$H]PABA relative to controls. From this data, it can be estimated that the growth inhibitory concentration of N-[2,4-diaminopteridin-6-yl) methyldibenz[b,f]azepine against *P. carinii* in an established culture is about 10 micromolar or less depending on the length of treatment.

EXAMPLE 74

Inhibition of dihydrofolate reductase (DHFR) from *Mycobacterium avium*

Compounds of the invention were tested for inhibition of dihydrofolate reductase (DHFR) from *Mycobacterium avium* (*M. avium*), an organism which has been used to screen drug candidates for activity against *tuberculosis*. IC$_{50}$ values were determined, which is the concentration (:M) of a compound required to inhibit the specified dihydrofolate reductase activity by 50%. Selectivity ratios also are were determined and set forth in the table, which are calculated as the ratio of IC$_{50}$ rat liver to IC$_{50}$ *M. avium*. The DHFR inhibition assay was conducted by the procedures disclosed in Broughton, M. C. et al., *Antimicrob. Agents Chemother.*, 1991, 35: 1348–1355; Chio, L. C. et al., *Antimicrob. Agents Chemother.*, 1993, 37: 1914–1923. Results are set forth in Table 2 below, with the tested compound identified by reference to the structural formula set forth at the top of the table (substituent X specified in Table 2), IC$_{50}$ values (expressed in:M) against rat liver DHFR and *M. avium* DHFR, followed by the selectivity index.

TABLE 2

Inhibition of dihydrofolate reductase from *Mycobacterium avium*

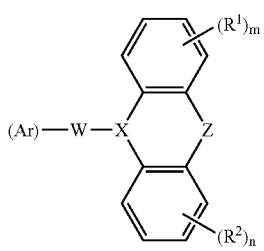

| Cmpd | X | rat liver DHFR | M. avium DHFR | Selectivity Index |
|---|---|---|---|---|
| 1 | CH=CH | 2.1 | 0.012 | 175 |
| 2 | a | 4.0 | 3.7 | 1.1 |
| 3 | $CH_2$ | 0.027 | 0.017 | 1.6 |
| 4 | O | 13 | 2.5 | 5.2 |
| 5 | S | 0.20 | 0.029 | 6.9 |

[a] No bridge between the phenyl rings (i.e. X is non-linked hydrogens)

The invention has been described in detail with reference to preferred embodiments thereof. However, it will be appreciated that those skilled in the art, upon consideration of this disclosure, may make modifications and improvements within the spirit and scope of the invention as set forth in the following claims.

What is claimed is:

1. A compound of the following Formula I:

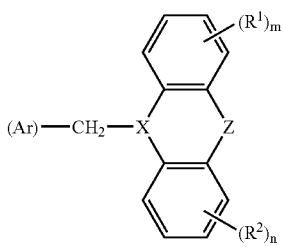

I wherein Ar is an optionally substituted heteroaromatic group having at least one amino substituent;

W is a chemical bond, optionally substituted amino, optionally substituted alkylene having 1 to 3 carbon atoms, or aminoalkylene having 1 nitrogen and 1 or 2 carbon atoms;

X is nitrogen;

Z represents optionally substituted ethylene or optionally substituted vinyl;

each $R^1$ and $R^2$ independently may be halogen, amino, hydroxy, nitro, azido, optionally substituted alkyl, optionally substituted alkenyl, optionally substituted alkynyl, optionally substituted alkoxy, optionally substituted aminoalkyl, optionally substituted alkanoyl, optionally substituted alkylthio, optionally substituted alkylsulfinyl, optionally substituted alkylsulfonyl, optionally substituted carbocyclic aryl, or optionally substituted heteroaromatic, or optionally substituted heteroalicyclic;

m and n are each independently an integer of from 0 to 4; and pharmaceutically acceptable salts thereof.

2. A compound of the following Formula II:

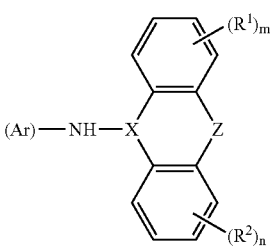

II wherein Ar is an optionally substituted heteroaromatic group having at lease one amino substituent;

Z represents optionally substituted ethylene, or optionally substituted vinyl;

X is nitrogen;

each $R^1$ and $R^2$ independently may be halogen, amino, hydroxy, nitro, azido, optionally substituted alkyl, optionally substituted alkenyl, optionally substituted alkynyl, optionally substituted alkoxy, optionally substituted aminoalkyl, optionally substituted alkanoyl, optionally substituted alkylthio, optionally substituted alkylsulfinyl, optionally substituted alkylsulfonyl, optionally substituted carbocyclic aryl, or optionally substituted heteroaromatic, or optionally substituted heteroalicyclic;

m and n are each independently an integer of from 0 to 4; and pharmaceutically acceptable salts thereof.

3. A compound of the following Formula IIA:

IIA (Ar)—NH—X—[structure with $(R^1)_m$ and $(R^2)_n$ and Z]

wherein Ar is optionally substituted carbocyclic aryl or optionally substituted heteroaromatic;

Z represents optionally substituted ethylene or optionally substituted vinyl;

X is nitrogen;

each $R^1$ and $R^2$ independently may be halogen, amino, hydroxy, nitro, azido, optionally substituted alkyl, optionally substituted alkenyl, optionally substituted alkynyl, optionally substituted alkoxy, optionally substituted aminoalkyl, optionally substituted alkanoyl, optionally substituted alkylthio, optionally substituted alkylsulfinyl, optionally substituted alkylsulfonyl, optionally substituted carbocyclic aryl, or optionally substituted heteroaromatic, or optionally substituted heteroalicyclic;

m and n are each independently an integer of from 0 to 4; and pharmaceutically acceptable salts thereof.

4. A compound of the following Formula III:

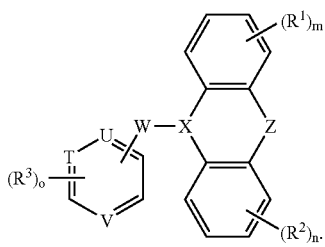

T, U and V are each independently optionally substituted carbon, or nitrogen wherein at least one of T, U, or V is optionally substituted nitrogen;

W is a chemical bond, optionally substituted amino, optionally substituted alkylene having 1 to 3 carbon atoms, or aminoalkylene having 1 nitrogen and 1 or 2 carbon atoms;

X is nitrogen;

Z represents optionally substituted ethylene or optionally substituted vinyl;

each $R^1$, $R^2$ and $R^3$ independently may be halogen, amino, hydroxy, nitro, azido, optionally substituted alkyl, optionally substituted alkenyl, optionally substituted alkynyl, optionally substituted alkoxy, optionally substituted aminoalkyl, optionally substituted alkanoyl, optionally substituted alkylthio, optionally substituted alkylsulfinyl, optionally substituted alkylsulfonyl, optionally substituted carbocyclic aryl, or optionally substituted heteroaromatic, or optionally substituted heteroalicyclic, wherein at least one occurrence of $R^3$ is an amino group;

m and n are each independently an integer of from 0 to 4;

o is an integer of from 1 to 5 and pharmaceutically acceptable salts thereof.

5. A compound of the following Formula IV:

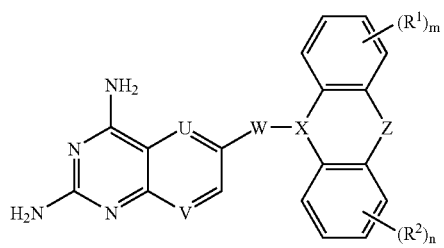

U and V are each independently optionally substituted carbon, or optionally substituted nitrogen;

W is a chemical bond, optionally substituted amino, optionally substituted alkylene having 1 to 3 carbon atoms, or aminoalkylene having nitrogen and 1 or 2 carbon atoms;

X is nitrogen;

Z represents optionally substituted ethylene or optionally substituted vinyl;

each $R^1$ and $R^2$ independently may be halogen, amino, hydroxy, nitro, azido, optionally substituted alkyl, optionally substituted alkenyl, optionally substituted alkynyl, optionally substituted alkoxy, optionally substituted aminoalkyl, optionally substituted alkanoyl, optionally substituted alkylthio, optionally substituted alkylsulfinyl, optionally substituted alkylsulfonyl, optionally substituted carbocyclic aryl, or optionally substituted heteroaromatic, or optionally substituted heteroalicyclic;

m and n are each independently an integer of from 0 to 4; and pharmaceutically acceptable salts thereof.

6. A compound of the following Formula IVA:

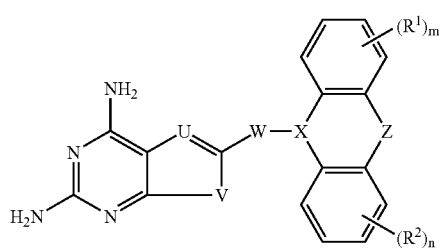

U and V are each independently optionally substituted carbon, or optionally substituted nitrogen; or V is O or S;

W is a chemical bond, optionally substituted amino, optionally substituted alkylene having 1 to 3 carbon atoms, or aminoalkylene having 1 nitrogen and 1 or 2 carbon atoms;

X is nitrogen;

Z represents optionally substituted ethylene or optionally substituted vinyl;

each $R^1$ and $R^2$ independently may be halogen, amino, hydroxy, nitro, azido, optionally substituted alkyl, optionally substituted alkenyl, optionally substituted alkynyl, optionally substituted alkoxy, optionally substituted aminoalkyl, optionally substituted alkanoyl, optionally substituted alkylthio, optionally substituted alkylsulfinyl, optionally substituted alkylsulfonyl, optionally substituted carbocyclic aryl, or optionally substituted heteroaromatic, or optionally substituted heteroalicyclic;

m and n are each independently all integer of from 0 to 4; and pharmaceutically acceptable salts thereof.

7. A compound of any one of claims 1, 2, 3, 4, 5 or 6 wherein Z is —$CH_2CH_2$—.

8. A compound of any one of claims 1, 4, 5 or 6 wherein W is a bond, $CH_2$, $CH_2CH_2$, or NH.

9. A compound of claim 1 selected from the group consisting of:

N-[(2,4-diaminopteridin-6-yl)methyl]-9,10-dihydrodibenz[b,f]azepine;

N-[(2,4-diaminopteridin-6-yl)methyl]dibenz[b,f]azepine;

N-[(2,4-diaminopyrido[2,3-d]pyrimidin-6-yl)methyl]-9,10-dihydrodibenz[b,f]azepine;

N-[(2,4-diaminopyrido[3,2-d]pyrimidin-6-yl)methyl]-9,10-dihydrodibenz[b,f]azepine;

N-[(2,4-diaminoquinazolin-6-yl)methyl]-9,10-dihydrodibenz[b,f]azepine;

N-[(2,4-diaminothieno[2,3-d]pyrimidin-5-yl)methyl]-9,10-dihydrodibenz[b,f]azepine;

N-[(2,4-diaminofuro[2,3-d]pyrimidin-5-yl)methyl]-9,10-dihydrodibenz[b,f]azepine;

N-[(2,4-diaminopyrimidin-5-yl)methyl]-9,10-dihydrodibenz[b,f]azepine;

N-[(2,4-diaminopyrido[2,3-d]pyrimidin-6-yl)methyl]dibenz[b,f]azepine;

N-[(2,4-diaminopyrido[3,2-d]pyrimidin-6-yl)methyl]dibenz[b,f]azepine;

N-[(2,4-diaminoquinazolin-6-yl)methyl]dibenz[b,f]azepine;

N-[(2,4-diaminothieno[2,3-d]pyrimidin-5-yl)methyl]dibenz[b,f]azepine;

N-[(2,4-diaminofuro[2,3-d]pyrimidin-5-yl)methyl]dibenz[b,f]azepine;

N-[(2,4-diaminopyrimidin-6-yl)methyl]dibenz[b,f]azepine, and pharmaceutically acceptable salts thereof.

10. A pharmaceutical composition comprising a pharmaceutically acceptable carrier and a compound of any one of claims 1, 3–7 or 9.

11. A method of treating a patient suffering from a parasitic disease, comprising administering to the patient an effective amount of a compound of claim 1 or claim 9, wherein the patient's immune system is suppressed.

12. A method of treating a patient suffering from toxoplasmosis, comprising administering to the patient all effective amount of a compound of claim 1 or claim 9, wherein the patient's immune system is suppressed.

13. The method of claim 11 wherein the patient has a retrovirus injection.

14. The method of claim 11 wherein the patient has an HIV infection.

15. The method of claim 11 wherein the patient is suffering from AIDS.

16. The method of claim 11 wherein the patient has received or is receiving immunosuppressive cancer chemotherapy treatment.

17. A method of treating a patient suffering from cryptosporidiosis, leischmaniasis or malaria, comprising administering to the patient an effective amount of a compound of claim 1 or claim 9, wherein the patient's immune system is suppressed.

18. A method of treating a patient suffering from an infection of *Toxoplasma gondii, Pnemocytis carinii, Cryptosporidium, Leishmania, Plasmodium vivax, P. falciparum, P. malarie,* or *P. ovale*, comprising administering to the patient an effective amount of a compound of claim 1 or claim 9, wherein the patient's immune system is suppressed.

19. A method of treating a patient suffering from a *Toxoplasma gondii* infection, comprising administering to the patient an effective amount of a compound of claim 1 or claim 9, wherein the patient's immune system is suppressed.

20. A method of treating a patient suffering from *tuberculosis*, comprising administering to the patient an effective amount of a compound of claim 1 or claim 9, wherein the patient's immune system is suppressed.

21. A method of claim 11 wherein the disease is treated without administration of a sulfa drug to the patient.

22. The method of claim 11 wherein the patient is a mammal.

23. The method of claim 11 wherein the patient is a human.

24. A method of claim 11 wherein the patient is a livestock animal, poultry or a domesticated animal.

25. The method of claim 12 wherein the patient has a retrovirus infection.

26. The method of claim 12 wherein the patient has an HIV infection.

27. The method of claim 12 wherein the patient is suffering from AIDS.

28. The method of claim 12 wherein the patient is a human.

29. The method of claim 19 wherein the patient is a human.

30. The method of claim 12 wherein the patient is a livestock animal, poultry or a domesticated animal.

31. The method of claim 19 wherein the patient is a livestock animal, poultry or a domesticated animal.

* * * * *